(12) United States Patent
Noda et al.

(10) Patent No.: US 9,248,060 B2
(45) Date of Patent: Feb. 2, 2016

(54) ABSORBENT ARTICLE

(71) Applicant: UNICHARM CORPORATION, Shikokuchuo-shi, Ehime (JP)

(72) Inventors: Yuki Noda, Kanonji (JP); Tatsuya Tamura, Kanonji (JP); Akira Hashino, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/430,420

(22) PCT Filed: Sep. 11, 2013

(86) PCT No.: PCT/JP2013/074574
§ 371 (c)(1),
(2) Date: Mar. 23, 2015

(87) PCT Pub. No.: WO2014/050573
PCT Pub. Date: Apr. 3, 2014

(65) Prior Publication Data
US 2015/0223997 A1    Aug. 13, 2015

(30) Foreign Application Priority Data

Sep. 28, 2012    (JP) .................................. 2012-218838

(51) Int. Cl.
*A61F 13/15* (2006.01)
*A61F 13/511* (2006.01)
(Continued)

(52) U.S. Cl.
CPC ..... *A61F 13/51113* (2013.01); *A61F 13/15699* (2013.01); *A61F 13/476* (2013.01);
(Continued)

(58) Field of Classification Search
CPC ................... A61F 13/51104; A61F 13/51108; A61F 13/51113; A61F 13/8405; A61F 2013/15284; A61F 2013/51066; A61F 2013/51069; A61F 2013/51117; A61F 2013/8455; A61F 2013/8461
See application file for complete search history.

(56) References Cited

U.S. PATENT DOCUMENTS 5,891,126 A    4/1999    Osborn, III et al.
6,120,488 A *  9/2000    VanRijswijck ....... A61F 13/494
                                                          604/364

(Continued)

FOREIGN PATENT DOCUMENTS

CN    101001650 A    7/2007
JP    2000-512886 A   10/2000
(Continued)

OTHER PUBLICATIONS

International Search Report mailed Dec. 17, 2013 in International Application No. PCT/JP2013/074574 filed Sep. 11, 2013.
(Continued)

*Primary Examiner* — Lynne Anderson
(74) *Attorney, Agent, or Firm* — Hauptman Ham, LLP

(57) ABSTRACT

An absorbent article includes a liquid-permeable top sheet, a liquid-impermeable back sheet, and an absorbent body that is arranged between the top sheet and the back sheet. The absorbent article further includes a pair of flaps provided to both sides of the absorbent article in a lengthwise direction, a first area containing a blood lubricity-imparting agent, and a second area containing a blood lubricity-imparting agent. The first and second areas are provided to at least an excretory orifice contact area of the top sheet and to the pair of flaps. A basis weight of the blood lubricity-imparting agent in the first area is greater than the basis weight of the blood lubricity-imparting agent in the second area.

15 Claims, 7 Drawing Sheets

(51) Int. Cl.
 *A61L 15/42* (2006.01)
 *A61L 15/50* (2006.01)
 *A61F 13/476* (2006.01)
 *A61F 13/84* (2006.01)

(52) U.S. Cl.
 CPC ............ *A61F13/8405* (2013.01); *A61L 15/42* (2013.01); *A61L 15/50* (2013.01); *A61F 2013/15284* (2013.01); *A61L 2420/00* (2013.01)

(56) References Cited

U.S. PATENT DOCUMENTS

| | | | |
|---|---|---|---|
| 6,603,053 B2* | 8/2003 | Hisanaka | A61F 13/4942 604/367 |
| 7,781,641 B2* | 8/2010 | Kasai | A61F 13/511 604/360 |
| 2003/0206843 A1 | 11/2003 | Nelson, Jr. | |
| 2005/0096614 A1 | 5/2005 | Perez et al. | |
| 2006/0036223 A1 | 2/2006 | Baldwin et al. | |
| 2007/0286876 A1 | 12/2007 | Warren et al. | |
| 2008/0010795 A1 | 1/2008 | Mizutani et al. | |
| 2008/0200894 A1 | 8/2008 | Gatto et al. | |
| 2008/0286224 A1 | 11/2008 | Vega et al. | |
| 2009/0221978 A1 | 9/2009 | Gatto et al. | |
| 2012/0226250 A1 | 9/2012 | Sato et al. | |
| 2014/0052086 A1 | 2/2014 | Komatsu et al. | |
| 2014/0358102 A1 | 12/2014 | Komatsu et al. | |

FOREIGN PATENT DOCUMENTS

| | | |
|---|---|---|
| JP | 2005-504591 A | 2/2005 |
| JP | 2007-509695 A | 4/2007 |
| JP | 2008-002034 A | 1/2008 |
| JP | 2008-503323 A | 2/2008 |
| JP | 2010-518918 A | 6/2010 |
| JP | 2010-526629 A | 8/2010 |
| JP | 2011-510801 A | 4/2011 |
| JP | 2011-131044 A | 7/2011 |
| JP | 2012-236001 A | 12/2012 |
| JP | 5122007 B1 | 1/2013 |
| WO | 98/55158 A2 | 12/1998 |
| WO | 03/028776 A1 | 4/2003 |
| WO | 2005-044164 A1 | 5/2005 |
| WO | 2006-009996 A1 | 1/2006 |
| WO | 2008/101163 A2 | 8/2008 |
| WO | 2008-139425 A1 | 11/2008 |
| WO | 2009-102837 A2 | 8/2009 |
| WO | 2012-133724 A1 | 10/2012 |
| WO | 2013-150924 A1 | 10/2013 |

OTHER PUBLICATIONS

Atsushi Fujita, "Prediction of Organic Compounds and Organic Conceptual Diagram," Journal of Japanese Chemistry, vol. 11, No. 10, Oct. 1957, pp. 719-725.

* cited by examiner (a)

50μm (b)

50μm

ABSORBENT ARTICLE

RELATED APPLICATIONS

The present application is a National Phase of International Application Number PCT/JP2013/074574, filed Sep. 11, 2013, which claims priority to Japanese Application Number 2012-218838, filed Sep. 28, 2012.

TECHNICAL FIELD

The present disclosure relates to an absorbent article.

BACKGROUND ART

As the basic performance of absorbent articles, such as sanitary napkins and panty liners has continued to improve with technological development over many years, leakage after absorption of excreta, such as menstrual blood has become a less frequent occurrence than in the past, and research is currently ongoing with the aim of achieving even higher performance, including a feel similar to underwear, and smoothness of the top sheet even after absorption of excreta, such as menstrual blood.

Menstrual blood during menstruation, in particular, can also contain components of the endometrium which are highly viscous, and the top sheet preferably remains smooth and stick-free even after absorption of such highly viscous menstrual blood. Highly viscous menstrual blood usually remains on the top sheet in the form of masses, generally leaving the user with a visually unpleasant image, and therefore from this viewpoint as well it is preferred for no highly viscous menstrual blood to remain on the top sheet.

Also, in an absorbent article, such as a sanitary napkin, it is common to employ a pair of flaps, such as a pair of side flaps or a pair of hip flaps, so that the sanitary napkin does not shift from shorts during use. For example, side flaps are folded to the back sheet side and anchored to the outer side of shorts to further prevent shifting of the sanitary napkin.

However, when the sanitary napkin has absorbed a large amount of menstrual blood, or when pressure has been applied to the sanitary napkin by twisting of the body or the like, the absorbed menstrual blood flows in the widthwise direction of the absorbent article and migrates to the side flaps, and the menstrual blood also seeps out from the side flaps, often soiling the thighs of the wearer.

Absorbent articles are known in the technical field which are coated with lotion compositions.

For example, PTL 1 discloses an absorbent article having a polypropylene glycol material-containing lotion composition situated on the inner surface of the top sheet (the clothing side surface), the inner surface of the back sheet (the body side surface), and on the base material between the inner surface of the top sheet and the inner surface of the back sheet.

Also, PTL 2 discloses an absorbent article wherein a polypropylene glycol material-containing lotion composition is applied on the outer surface of the top sheet (body side surface).

CITATION LIST

Patent Literature

PTL 1 Japanese Unexamined Patent Publication No. 2010-518918
PTL 2 Japanese Unexamined Patent Publication No. 2011-510801

SUMMARY OF INVENTION

Technical Problem

For the absorbent articles described in PTLs 1 and 2, nothing is mentioned regarding preventing absorbed menstrual blood from seeping from the flaps.

It is therefore an object of the present disclosure to provide an absorbent article with low stickiness and a light feel after the excretory opening contact region of the top sheet has absorbed menstrual blood, and with low seepage of absorbed menstrual blood from the flaps.

Solution to Problem

As a result of diligent research directed toward solving the problems described above, the present inventors have discovered an absorbent article having a liquid-permeable top sheet, a liquid-impermeable back sheet and an absorbent body between the top sheet and the back sheet, wherein the absorbent article comprises, at both sides in the lengthwise direction, a pair of flaps for anchoring the absorbent article to a clothing of a wearer, and at least an excretory opening contact region of the top sheet and the pair of flaps have a blood slipping agent-containing first region and blood slipping agent-containing second regions each containing a blood slipping agent with a kinematic viscosity of 0.01 to 80 mm$^2$/s at 40° C., a water holding percentage of 0.01 to 4.0 mass % and a weight-average molecular weight of less than 1,000, a basis weight of the blood slipping agent in the blood slipping agent-containing first region in the excretory opening contact region of the top sheet is greater than a basis weight of the blood slipping agent in the blood slipping agent-containing second regions in the pair of flaps.

Advantageous Effects of Invention

The absorbent article of this disclosure has low stickiness and a light feel after the excretory opening contact region of the top sheet has absorbed menstrual blood, and low seepage of absorbed menstrual blood from the flaps.

DESCRIPTION OF EMBODIMENTS

Definitions

Some of the terms used throughout the present specification will now be defined.

"Excretory Opening Contact Region"

As used herein, "excretory opening contact region" of the top sheet means the region of the top sheet that contacts with the excretory opening (labia minora, etc.) of the wearer. The excretory opening contact region will have a different location depending on the size of the absorbent article, and for an absorbent article with side flaps, the excretory opening contact region will usually be the inner side of the region defined by embossing disposed in a continuous or discontinuous manner surrounding a lengthwise line running through the widthwise center of the absorbent article, and the intersection with a widthwise line running through the lengthwise centers of both wing sections. Also, in the case of an absorbent article without side flaps, usually the excretory opening contact region is defined by embossing that is disposed continuously or discontinuously surrounding the widthwise center section and the lengthwise center section of the absorbent article.

"Flaps"

Throughout the present specification, "flaps" means members situated on both sides in the lengthwise direction of the absorbent article, and serving to anchor the absorbent article to the clothing of the wearer.

Examples of flaps include side flaps situated on both sides in the lengthwise direction of the absorbent article at the excretory opening contact region, and hip flaps situated on both sides in the lengthwise direction of the absorbent article at the back of the absorbent article. Side flaps and hip flaps are sometimes separate and distinguishable, or are sometimes continuous and non-distinguishable.

Also, side flaps are usually folded on the back sheet side and anchored to the outer side of shorts using an adhesive section, while hip flaps are usually not folded and anchored to the inner side of shorts using an adhesive section.

The term "flaps" as used herein includes side flaps and hip flaps.

"Front" and "Back"

Throughout the present specification, "front" and "back" are in reference to the wearer, and mean the front of the wearer and the back of the wearer, respectively.

"Skin Side Sheet" and "Clothing Side Sheet"

The "skin side sheet" and "clothing side sheet" of the flaps refer respectively to the liquid-permeable top sheet and liquid-impermeable back sheet of the absorbent article, when the absorbent article is in an opened state.

The absorbent article of this disclosure will now be explained in detail.

Figure 1:
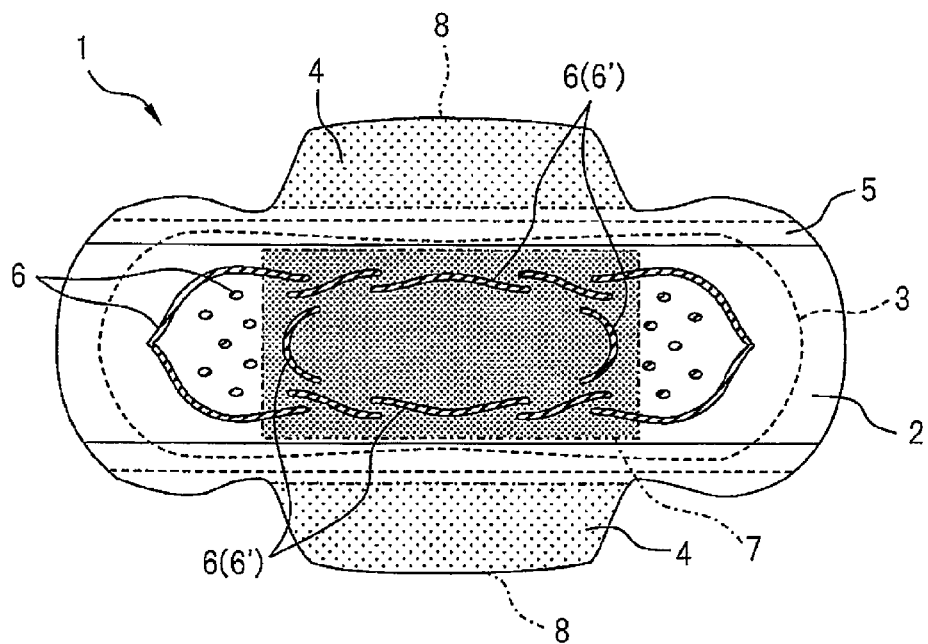
FIG. 1 is a front view of an absorbent article according to an embodiment of the present disclosure.

FIG. 1 is a front view of an absorbent article, and more specifically a front view of a sanitary napkin, according to an embodiment of this disclosure. FIG. 1 is as observed from the skin contact side of the top sheet 2. The absorbent article 1 shown in FIG. 1 has a liquid-permeable top sheet 2, a liquid-impermeable back sheet (not shown), and an absorbent body 3 between the top sheet 2 and the back sheet. In the absorbent article 1 shown in FIG. 1, a pair of flaps, and more specifically a pair of side flaps 4, are provided on both sides in the lengthwise direction of the absorbent article 1, to anchor the absorbent article 1 to the clothing of the wearer, such as shorts. The pair of side flaps 4 extend to the outer side of the absorbent article 1 at both sides of the absorbent article 1 at the excretory opening contact region.

In the absorbent article 1 shown in FIG. 1, the left side is the front.

In the absorbent article 1 shown in FIG. 1, the excretory opening contact region is the region defined by four embossings 6' within the blood slipping agent-containing first region 7, and all of the excretory opening contact regions of the top sheet 2 have a blood slipping agent-containing first region 7.

The absorbent article 1 shown in FIG. 1 has a side sheet 5 and a plurality of embossings 6, but the absorbent article according to another embodiment of this disclosure lacks either or both a side sheet and/or embossing.

In FIG. 1, the top sheet 2 is formed of a nonwoven fabric, but in an absorbent article according to another embodiment of this disclosure, the top sheet is formed of a woven fabric or porous film.

In the absorbent article 1 shown in FIG. 1, at least the excretory opening contact region of the top sheet 2 and the pair of side flaps 4 have a blood slipping agent-containing first region 7 and blood slipping agent-containing second regions 8 each containing a blood slipping agent having a kinematic viscosity of 0.01 to 80 mm$^2$/s at 40° C., a water holding percentage of 0.01 to 4.0 mass % and a weight-average molecular weight of less than 1,000. In the absorbent article 1 shown in FIG. 1, the basis weight of the blood slipping agent in the blood slipping agent-containing first region 7 in the excretory opening contact region of the top sheet 2 is greater than the basis weight of the blood slipping agent in the blood slipping agent-containing second regions 8 of the pair of side flaps 4.

The blood slipping agent will be described below.

Figure 2:
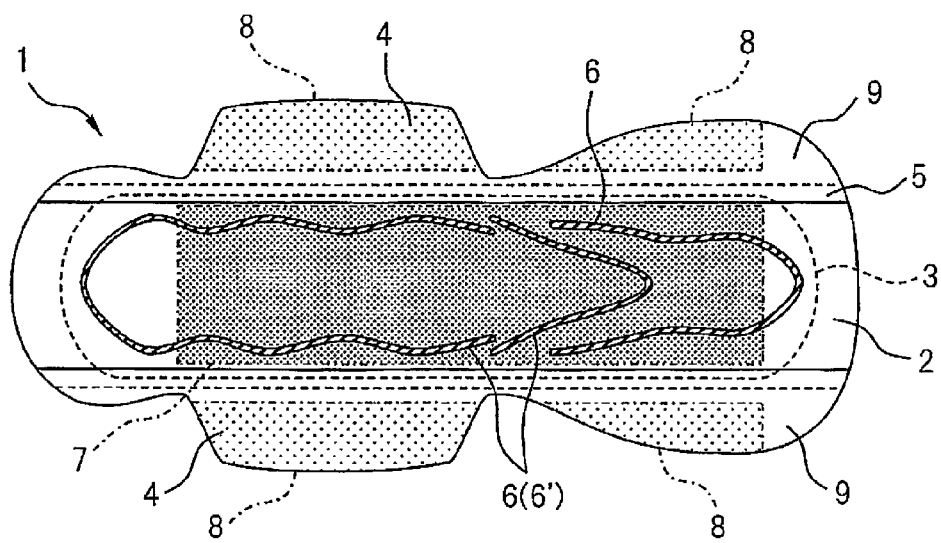
FIG. 2 is a front view of an absorbent article according to another embodiment of the present disclosure.

FIG. 2 is a front view of an absorbent article, and more specifically a front view of a sanitary napkin, according to another embodiment of this disclosure. FIG. 2 is as observed from the skin contact side of the top sheet 2. The absorbent article 1 shown in FIG. 2 has a liquid-permeable top sheet 2, a liquid-impermeable back sheet (not shown), and an absorbent body 3 between the top sheet 2 and the back sheet. In the absorbent article 1 shown in FIG. 2, a pair of flaps, and more specifically a pair of side flaps 4, and a pair of hip flaps 9, are further provided on both sides in the lengthwise direction of the absorbent article 1, to anchor the absorbent article 1 to the clothing of the wearer. In the absorbent article 1 shown in FIG. 2, the pair of side flaps 4 extend toward the outer sides of the absorbent article 1, at both sides of the absorbent article 1 at the excretory opening contact region, and the pair of hip flaps 9 extend toward the outer sides of the absorbent article 1, at both sides in the lengthwise direction of the absorbent article 1 at the back of the absorbent article 1.

In the absorbent article 1 shown in FIG. 2, the left side is the front.

Also, in the absorbent article 1 shown in FIG. 2, the excretory opening contact region is the region delineated by two embossings 6', within the blood slipping agent-containing first region.

The absorbent article 1 shown in FIG. 2 has a side sheet 5 and a plurality of embossings 6, but the absorbent article according to another embodiment of this disclosure lacks either or both a side sheet and/or embossing.

In the absorbent article 1 shown in FIG. 2, the top sheet 2 is formed of a nonwoven fabric, but in an absorbent article according to another embodiment of this disclosure, the top sheet 2 is formed of a woven fabric or porous film.

In the absorbent article 1 shown in FIG. 2, at least the excretory opening contact region of the top sheet 2 has a blood slipping agent-containing first region 7 containing a blood slipping agent, and the pair of side flaps 4 and the pair of hip flaps 9 each have blood slipping agent-containing second regions 8 containing a blood slipping agent. In the absorbent article 1 shown in FIG. 2, the basis weight of the blood slipping agent in the blood slipping agent-containing first region 7 of the excretory opening contact region of the top sheet 2 is greater than the basis weight of the blood slipping agent in the blood slipping agent-containing second regions 8 of the pair of side flaps 4 and the pair of hip flaps 9.

In the absorbent article 1 shown in FIG. 2, the pair of side flaps 4 and the pair of hip flaps 9 both have blood slipping agent-containing second regions 8 containing a blood slipping agent, but in an absorbent article according to another embodiment of this disclosure, only the pair of side flaps or the pair of hip flaps have blood slipping agent-containing second regions, i.e., the pair of side flaps have blood slipping agent-containing second regions or the pair of hip flaps have blood slipping agent-containing second regions.

In the absorbent article of this disclosure, the top sheet contains the blood slipping agent in the blood slipping agent-containing first region at a basis weight in a range of preferably about 1 to about 30 g/m$^2$, more preferably about 2 to about 20 g/m$^2$ and even more preferably about 3 to about 10 g/m$^2$. The action of the blood slipping agent will be described below, but if the basis weight is lower than about 1 g/m$^2$, menstrual blood that has reached the excretory opening contact region of the top sheet will tend to remain there without rapidly migrating into the absorbent body, while if the basis weight is greater than about 30 g/m$^2$, a greater degree of stickiness will tend to be felt when the article is worn.

In the absorbent article of this disclosure, the top sheet has a blood slipping agent-containing first region containing a blood slipping agent in at least the excretory opening contact region, but it may also have a blood slipping agent-containing first region in regions other than the excretory opening contact region. For example, in an absorbent article according to one embodiment of this disclosure, the top sheet has a blood slipping agent-containing first region containing a blood slipping agent only in the excretory opening contact region. Also, in an absorbent article according to another embodiment of this disclosure, the top sheet has a blood slipping agent-containing first region containing a blood slipping agent throughout the entire top sheet beyond the excretory opening contact region.

In the absorbent article of this disclosure, the pair of flaps each contain the blood slipping agent in the blood slipping agent-containing second regions at a basis weight that is in a proportion of preferably about 1 to about 70 mass %, more preferably about 3 to about 60 mass % and even more preferably about 5 to about 50 mass % of the basis weight of the blood slipping agent in the blood slipping agent-containing first region of the excretory opening contact region of the top sheet.

The pair of flaps may be a pair of side flaps or one hip flap, as described above.

The effect of the blood slipping agent will be described below, but if the proportion is less than about 1 mass %, menstrual blood that has migrated from the interior of the absorbent article to the flaps will be repelled, the force pushing it back in the direction of the absorbent body will be weakened, and menstrual blood may seep out from the flaps. Also, if the proportion falls below about 1 mass %, menstrual blood that has reached the flaps may be repelled through the surface of the absorbent article, the force pushing it back to the top sheet will be weakened, and this may lead to leakage.

A proportion of greater than about 70 mass % will lower the tack of the adhesive bonding together the materials composing the flaps, tending to result in separation of the materials when worn. Furthermore, a proportion of greater than about 70 mass % may cause the blood slipping agent in the flaps to migrate and touch the crotch of the wearer, creating a feeling of discomfort for the wearer.

The basis weight of the blood slipping agent in the top sheet, referred to throughout the present specification, is measured in the following manner.

(1) The region of the top sheet that is to be measured is cut out using a sharp blade, such as a cutter replacement blade, while avoiding alteration in thickness, to obtain a sample.

(2) The area of the sample: SA (m$^2$) and the mass: $SM_0$ (g) are measured.

(3) The sample is stirred for at least 3 minutes in a solvent that can dissolve the blood slipping agent, such as ethanol or acetone, to dissolve the blood slipping agent in the solvent.

(4) The sample is filtered on mass-measured filter paper, and the sample is thoroughly rinsed with the solvent on the filter paper. The sample on the filter paper is dried in an oven at 60° C.

(5) The masses of the filter paper and sample are measured, and the mass of the filter paper is subtracted to calculate the dry sample mass: $SM_1$ (g).

(6) The basis weight BBS (g/m$^2$) of the blood slipping agent is calculated by the following formula.

$$BBS\,(g/m^2) = [SM_0\,(g) - SM_1\,(g)] / SA\,(m^2)$$

In order to minimize error, multiple samples are taken from multiple absorbent articles, without the total area of the sample exceeding 100 cm$^2$, conducting several repeated measurements and taking the average value.

In the absorbent article of this disclosure, the blood slipping agent-containing first region and the blood slipping agent-containing second regions may contain the same blood slipping agent, or they may contain the same combination of blood slipping agents. In addition, the blood slipping agent-containing second regions of the side flaps and the blood slipping agent-containing second regions of the hip flaps may contain the same blood slipping agent or they may contain the same combination of blood slipping agents.

In the absorbent article of this disclosure, the blood slipping agent-containing first region and the blood slipping agent-containing second regions may contain different blood slipping agents, or they may contain different combinations of blood slipping agents. In addition, the blood slipping agent-containing second regions of the side flaps and the blood slipping agent-containing second regions of the hip flaps may contain different blood slipping agents or they may contain different combinations of blood slipping agents.

For example, when the excretory opening contact region of the top sheet contains in the blood slipping agent-containing first region a blood slipping agent having a low water holding percentage, such as a water holding percentage of about 0.01 to about 3.0 mass %, about 0.01 to 2.0 mass % or about 0.01 to about 1.0 mass %, the affinity between the blood slipping agent and the hydrophilic components (blood plasma and other components) in menstrual blood is low, and this causes menstrual blood that has reached the excretory opening contact region to drop down into the absorbent article rapidly within this region.

Also, when the flaps contain a blood slipping agent in the blood slipping agent-containing second regions that have a water holding percentage that is higher than the blood slipping agent in the blood slipping agent-containing first region, such as a water holding percentage that is about 0.1 to about 0.5 mass %, about 0.2 to about 1.0 mass % or about 0.3 to about 1.5 mass % higher than the blood slipping agent in the blood slipping agent-containing first region, the affinity between the blood slipping agent and the hydrophilic components (such as blood plasma) in menstrual blood increases, and therefore the menstrual blood that has flowed over the surface of the top sheet and reached the skin side sheet of the flap is captured and migrates into the flaps, thereby preventing leakage of the menstrual blood.

In addition, when the flaps contain a blood slipping agent having a low water holding percentage, such as a water holding percentage of about 0.01 to about 3.0 mass %, about 0.01 to 2.0 mass % or about 0.01 to about 1.0 mass % in the blood slipping agent-containing second regions, the hydrophobicity of the flaps is further increased, and this further strengthens the force by which menstrual blood that has reached the flaps is repelled to the absorbent body, so that menstrual blood is pushed back to the absorbent body and is less likely to seep out from the flaps.

[Blood Slipping Agent]

In the absorbent article of this disclosure, at least the excretory opening contact region of the top sheet and the pair of flaps have a blood slipping agent-containing first region and blood slipping agent-containing second regions each containing a blood slipping agent having a kinematic viscosity of about 0.01 to about 80 mm$^2$/s at 40° C., a water holding percentage of about 0.05 to about 4.0 mass % and a weight-average molecular weight of less than about 1,000.

The blood slipping agent has, at 40° C., a kinematic viscosity of about 0 to about 80 mm$^2$/s, preferably a kinematic viscosity of about 1 to about 70 mm$^2$/s, more preferably a kinematic viscosity of about 3 to about 60 mm$^2$/s, even more preferably a kinematic viscosity of about 5 to about 50 mm$^2$/s, and yet more preferably a kinematic viscosity of about 7 to about 45 mm$^2$/s.

The kinematic viscosity tends to be higher with a) a larger molecular weight of the blood slipping agent, b) a higher percentage of polar groups, such as carbonyl bonds (—CO—), ether bonds (—O—), carboxyl groups (—COOH) and hydroxyl groups (—OH), and c) a larger IOB.

In order to have a kinematic viscosity of about 0 to about 80 mm$^2$/s at 40° C., the melting point of the blood slipping agent is preferably 45° C. or less. This is because the kinematic viscosity will tend to be higher if the blood slipping agent contains crystals at 40° C.

As used herein, the "kinematic viscosity at 40° C." may be referred to simply as "kinematic viscosity".

The significance of the kinematic viscosity of the blood slipping agent will be explained below, but a kinematic viscosity exceeding about 80 mm$^2$/s will tend to result in high viscosity of the blood slipping agent, so that the blood slipping agent will tend to be resistant to slipping into the absorbent article together with menstrual blood that has reached the skin contact surface of the top sheet. A kinematic viscosity exceeding about 80 mm$^2$/s will tend to inhibit the blood slipping agent from slipping down into the flaps together with menstrual blood that has reached the surface of the skin side sheet of the flaps.

The kinematic viscosity can be measured according to JIS K 2283:2000, "5. Kinematic Viscosity Test Method", using a Cannon-Fenske reverse-flow viscometer, at a testing temperature of 40° C.

The blood slipping agent has a water holding percentage of about 0.01 to about 4.0 mass %, preferably it has a water holding percentage of about 0.02 to about 3.5 mass %, more preferably it has a water holding percentage of about 0.03 to about 3.0 mass %, even more preferably it has a water holding percentage of about 0.04 to about 2.5 mass %, and yet more preferably it has a water holding percentage of about 0.05 to about 2.0 mass %.

As used herein, "water holding percentage" means the percentage (mass) of water that can be held by a substance, and it may be measured in the following manner.

(1) A 20 mL test tube, a rubber stopper, the substance to be measured and deionized water are allowed to stand for a day and a night in a thermostatic chamber at 40° C.

(2) Into the test tube in the thermostatic chamber there are charged 5.0 g of the substance to be measured and 5.0 g of deionized water.

(3) The mouth of the test tube is sealed with the rubber stopper in the thermostatic chamber, and the test tube is rotated once and allowed to stand for 5 minutes.

(4) A 3.0 g portion of the layer of the substance to be measured (usually the upper layer) is sampled into a glass dish with a diameter of 90 mm and a mass of $W_0$ (g), in the thermostatic chamber.

(5) The dish is heated at 105° C. for 3 hours in an oven to evaporate off the moisture, and the mass $W_1$ (g) of each dish is measured.

(6) The water holding percentage is calculated by the following formula.

Water holding percentage (mass %)=100×[$W_0$ (g)−$W_1$ (g)]/3.0 (g)

The measurement is conducted three times, and the average value is recorded.

The significance of the water holding percentage of the blood slipping agent will be explained below, but a low water holding percentage will tend to lower the affinity between the blood slipping agent and menstrual blood, thus helping to prevent menstrual blood that has reached the skin contact surface of the top sheet from slipping into the absorbent article. Also, if the water holding percentage is reduced menstrual blood that has reached the surface of the skin side sheet of the flaps will tend to less easily slip down into the interior of the flaps.

If the water holding percentage is high, on the other hand, the affinity with menstrual blood will become very high, similar to a surfactant, and absorbed menstrual blood will tend to remain on the skin contact surface of the top sheet and/or on the surface of the skin side sheet of the flaps, resulting in more red coloration of the skin contact surface of the top sheet.

The water holding percentage tends to be a larger value with a) a smaller molecular weight of the blood slipping agent, and b) a higher percentage of polar groups, such as carbonyl bonds (—CO—), ether bonds (—O—), carboxyl groups (—COOH) and hydroxyl groups (—OH). This is because the blood slipping agent has greater hydrophilicity. The water holding percentage will tend to have a larger value with a greater IOB, i.e with a higher inorganic value or with a lower organic value. This is because the blood slipping agent will have greater hydrophilicity.

The significance of the kinematic viscosity and water holding percentage of the blood slipping agent will now be explained with reference to FIG. 9.

Figure 9:
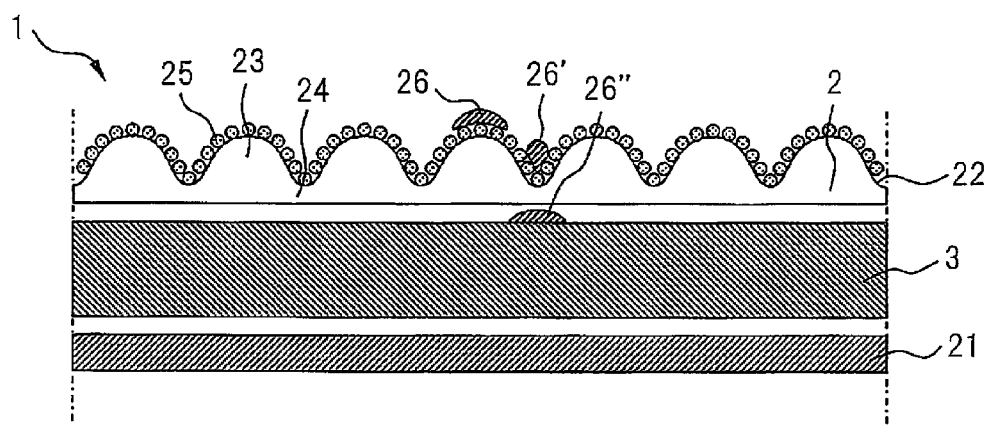
FIG. 9 is a diagram schematically illustrating migration of menstrual blood into an absorbent body by a blood slipping agent.

FIG. 9 is a diagram schematically illustrating migration of menstrual blood into an absorbent body by a blood slipping agent. FIG. 9 is a cross-sectional view of an absorbent article 1 comprising a liquid-permeable top sheet 2, a liquid-impermeable back sheet 21 and an absorbent body 3 between the liquid-permeable top sheet 2 and liquid-impermeable back sheet 21. In FIG. 9, the top sheet 2 is formed of a nonwoven fabric, and it has a plurality of projections 23 and a plurality of recesses 24 on the skin contact surface 22, with a blood slipping agent 25 coated on the skin contact surface 22 of the top sheet 2. In FIG. 9, the blood slipping agent 25 is shown as droplets (or particles) on the skin contact surface 22 of the top sheet 2 for convenience, but in the absorbent article of this disclosure, the form and distribution of the blood slipping agent is not limited to that shown in the drawing.

As shown in FIG. 9, menstrual blood 26 that has reached the projections 23 of the top sheet 2 contacts with the blood slipping agent 25 that is present in the projections 23. A portion of the blood slipping agent 25 present in the projections 23 slips down into the recesses 24 together with the menstrual blood 26 (menstrual blood 26'). The menstrual blood 26' then slips down into the recesses 24, reaching the absorbent body 3 (menstrual blood 26"). Next, the menstrual blood 26" is absorbed into the absorbent body 3.

More specifically, the blood slipping agent 25 having a water holding percentage of about 0.01 to about 4.0 mass % has a certain affinity with menstrual blood 26. For example, the hydrophilic portion of the blood slipping agent 25 (for example, a hydrophilic group, such as a polar group, for example, such as carbonyl, oxy, carboxyl, hydroxyl or the like, or a hydrophilic bond, such as a polar bond, for example, such as a carbonyl bond, ester bond, carbonate bond, ether bond or the like) has high affinity with the hydrophilic components (such as blood plasma) in the menstrual blood 26, and attracts the components with affinity, whereas the hydrophobic portion (for example, the hydrocarbon moiety) of the blood slipping agent 25 has low affinity with the hydrophilic components (such as blood plasma) in the menstrual blood 26 and repels the hydrophilic components, such that it functions as a "lubricant", causing the menstrual blood 26 to slip down toward the absorbent body 3.

Also, since the blood slipping agent 25 having a kinematic viscosity of about 0.01 to about 80 mm²/s at 40° C. has very low viscosity near the body temperature of the wearer, a portion thereof slips down from the projections 23 into the recesses 24 together with the menstrual blood 26, subsequently passing through the recesses 24 into the absorbent article 1.

Furthermore, since the blood slipping agent 25 has a water holding percentage of about 0.01 to about 4.0 mass %, its affinity with the hydrophilic components (such as blood plasma) in menstrual blood 26 is not excessively high, and this causes less of the menstrual blood 26 to remain on the top sheet 2. This is because the hydrophilic components (such as blood plasma) in the menstrual blood 26 repels the hydrophobic portion of the blood slipping agent 25.

FIG. 9 schematically illustrates migration of menstrual blood into the absorbent body by the blood slipping agent, for a top sheet 2 formed of a nonwoven fabric and having a plurality of projections 23 and a plurality of recesses 24 on the skin contact surface 22, but menstrual blood also migrates in the same manner in a top sheet without irregularities, such as a flat nonwoven fabric or woven fabric, a porous film or a flap-like skin side sheet.

This is because in a nonwoven fabric or woven fabric, the blood slipping agent causes the menstrual blood to slip down between the fibers, while in a porous film, the blood slipping agent causes the menstrual blood to slip down into the pores.

In addition, a blood slipping agent having a water holding percentage of about 0.01 to about 4.0 mass % in the flaps has low affinity mainly with the hydrophilic components in menstrual blood (blood plasma and the like) and has an effect of repelling menstrual blood, such that it repels menstrual blood that is attempting to migrate into the flaps from the interior of the absorbent article.

FIG. 9 schematically illustrates migration of menstrual blood into an absorbent body by a blood slipping agent, but a blood slipping agent-containing composition functions in the same manner.

The blood slipping agent has a weight-average molecular weight of less than about 1,000, and preferably a weight-average molecular weight of less than about 900. This is because, if the weight-average molecular weight is about 1,000 or higher, tack may result in the blood slipping agent itself, tending to create a feeling of unpleasantness for the wearer. If the weight-average molecular weight increases, the viscosity of the blood slipping agent will tend to increase, and it will therefore be difficult to lower the viscosity of the blood slipping agent by heating to a viscosity suitable for coating, and as a result, the blood slipping agent may need to be diluted with a solvent.

The blood slipping agent preferably has a weight-average molecular weight of about 100 or greater, and more preferably it has a weight-average molecular weight of about 200 or greater. This is because if the weight-average molecular weight is low, the vapor pressure of the blood slipping agent may be increased, gasification may occur during storage and the amount may be reduced, often leading to problems, such as odor during wear.

In addition, as used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ ($i=1$, or $i=1$, $2 \ldots$), it refers to $M_w$ determined by the following formula.

$$M_w = \Sigma N_i M_i^2 / \Sigma N_i M_i$$

As used herein, the weight-average molecular weights are the values measured by gel permeation chromatography (GPC), based on polystyrene.

The GPC measuring conditions may be the following, for example.

Device: Lachrom Elite high-speed liquid chromatogram by Hitachi High-Technologies Corp.

Columns: SHODEX KF-801, KF-803 and KF-804, by Showa Denko K.K.

Eluent: THF

Flow rate: 1.0 mL/min

Driving volume: 100

Detection: RI (differential refractometer)

The weight-average molecular weights listed in the examples of the present specification were measured under the conditions described below.

The blood slipping agent can have an IOB of about 0.00 to about 0.60.

The IOB (Inorganic Organic Balance) is an indicator of the hydrophilic-lipophilic balance, and as used herein, it is the value calculated by the following formula by Oda et al.:

$$IOB = \text{inorganic value/organic value}.$$

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725.

The organic values and inorganic values of major groups, according to Fujita, are summarized in Table 1 below.

TABLE 1

| Group | Inorganic value | Organic value |
|---|---|---|
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |
| Triple bond | 3 | 0 |
| Double bond | 2 | 0 |
| $CH_2$ | 0 | 20 |
| iso-branch | 0 | −10 |
| tert-branch | 0 | −20 |
| Light metal (salt) | ≥500 | 0 |
| Heavy metal (salt), amine, $NH_3$ salt | ≥400 | 0 |

For example, in the case of an ester of tetradecanoic acid which has 14 carbon atoms and dodecyl alcohol which has 12 carbon atoms, the organic value is 520 ($CH_2$, 20×26) and the inorganic value is 60 (—COOR, 60×1), and therefore IOB=0.12.

The IOB of the blood slipping agent is preferably between about 0.00 and 0.60, more preferably between about 0.00 and 0.50, even more preferably between about 0.00 and 0.40 and most preferably between about 0.00 and 0.30. If the IOB is within this range, it will be easier to meet the aforementioned conditions for the water-holding capacity and kinematic viscosity.

The blood slipping agent preferably has a melting point of no higher than 45° C., and more preferably it has a melting point of no higher than 40° C. If the blood slipping agent has a melting point of no higher than 45° C., the blood slipping agent will more easily exhibit a kinematic viscosity in the aforementioned range.

As used herein, the term "melting point" refers to the peak top temperature for the endothermic peak during conversion from solid to liquid, upon measurement with a differential scanning calorimetry analyzer at a temperature-elevating rate of 10° C./min. The differential scanning calorimetry analyzer used may be, for example, a DSC-60-type DSC measuring apparatus by Shimadzu Corp.

If the blood slipping agent has a melting point of about 45° C. or less, it may be either liquid or solid at room temperature (about 25° C.), or in other words, the melting point may be either about 25° C. or higher or below about 25° C., and for example, it may have a melting point of about −5° C. or about −20° C. The reason for a melting point of about 45° C. or less for the blood slipping agent will be explained below.

The blood slipping agent does not have a lower limit for the melting point, but the vapor pressure is preferably low. The vapor pressure of the blood slipping agent is preferably about 0-200 Pa, more preferably about 0-100 Pa, even more preferably about 0-10 Pa, even more preferably about 0-1 Pa, and even more preferably about 0.0-0.1 Pa at 25° C. (1 atmosphere).

Considering that the absorbent article of this disclosure is to be used in contact with the human body, the vapor pressure is preferably about 0-700 Pa, more preferably about 0-100 Pa, even more preferably about 0-10 Pa, even more preferably about 0-1 Pa, and even more preferably 0.0-0.1 Pa, at 40° C. (1 atmosphere). If the vapor pressure is high, gasification may occur during storage and the amount of blood slipping agent may be reduced, and as a consequence problems, such as odor during wear, may be created.

The melting point of the blood slipping agent may be selected depending on the weather or duration of wear. For example, in regions with a mean atmospheric temperature of about 10° C. or less, using a blood slipping agent with a melting point of about 10° C. or less may help the blood slipping agent function after excretion of menstrual blood, even if it has been cooled by the ambient temperature.

Also, when the absorbent article is to be used for a prolonged period of time, the melting point of the blood slipping agent is preferably at the high end of the range of about 45° C. or less. This is so that the blood slipping agent will not be easily affected by sweat or friction during wearing, and will not easily become biased even during prolonged wearing.

In the technical field, the skin contact surfaces of top sheets are coated with surfactants in order to alter the surface tension of menstrual blood and promote rapid absorption of menstrual blood. However, the top sheet coated with the surfactant has very high affinity for the hydrophilic components (blood plasma, etc.) in menstrual blood, and acts to attract them, tending to cause menstrual blood instead to remain on the top sheet. The blood slipping agent, unlike conventionally known surfactants, has low affinity with menstrual blood and therefore does not cause residue of menstrual blood on the top sheet and allows rapid migration into the absorbent body.

Preferably, the blood slipping agent is selected from the group consisting of following items (i)-(iii), and any combination thereof:

(i) a hydrocarbon;
(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen on the hydrocarbon moiety.

As used herein, "hydrocarbon" refers to a compound composed of carbon and hydrogen, and it may be a chain hydrocarbon, such as a paraffinic hydrocarbon (containing no double bond or triple bond, also referred to as alkane), an olefin-based hydrocarbon (containing one double bond, also referred to as alkene), an acetylene-based hydrocarbon (containing one triple bond, also referred to as alkyne), or a hydrocarbon comprising two or more bonds selected from the group consisting of double bonds and triple bonds, and cyclic hydrocarbon, such as aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include linear hydrocarbons and branched hydrocarbons.

When two or more oxy groups (—O—) are inserted in the compounds of (ii) and (iii) above, the oxy groups (—O—) are not adjacent each other. Thus, compounds (ii) and (iii) do not include compounds with continuous oxy groups (i.e., peroxides).

In the compounds of (iii), compounds in which at least one hydrogen on the hydrocarbon moiety is substituted with a hydroxyl group (—OH) are preferred over compounds in which at least one hydrogen on the hydrocarbon moiety is substituted with a carboxyl group (—COOH). This is because the carboxyl groups bond with metals and the like in menstrual blood, increasing the water holding percentage of the blood slipping agent, which may sometimes exceed the prescribed range. The same is true from the viewpoint of the IOB as well. As shown in Table 1, the carboxyl groups bond with metals and the like in menstrual blood, drastically increasing the inorganic value from 150 to 400 or greater, and therefore a blood slipping agent with carboxyl groups can increase the IOB value to more than about 0.60 during use.

More preferably, the blood slipping agent is selected from the group consisting of following items (i')-(iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety.

When 2 or more same or different bonds are inserted in the compound of (ii') or (iii'), i.e., when 2 or more same or different bonds selected from the group consisting carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood slipping agent has more preferably about 1.8 or less carbonyl bonds (—CO—), about 2 or less ester bonds (—COO—), about 1.5 or less carbonate bonds (—OCOO—), about 6 or less ether bonds (—O—), about 0.8 or less carboxyl groups (—COOH) and/or about 1.2 or less hydroxyl groups (—OH), per 10 carbon atoms in the hydrocarbon moiety.

Even more preferably, the blood slipping agent is selected from the group consisting of following items (A)-(F), and any combination thereof:

(A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;

(B) an ether of (B1) a compound having a chain hydrocarbon moiety and 2-4 hydroxyl groups substituting for hydrogens on the chain hydrocarbon moiety, and (B2) a compound having a chain hydrocarbon moiety and 1 hydroxyl group substituting for a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting for hydrogens on the chain hydrocarbon moiety, and (C2) a compound having a chain hydrocarbon moiety and 1 hydroxyl group substituting for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_3$-$C_6$ alkylene glycol, or ester or ether thereof; and (F) a chain hydrocarbon.

The blood slipping agent in accordance with (A) to (F) will now be described in detail.

[(A) Ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety]

In the (A) ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety (hereunder also referred to as "compound (A)"), it is not necessary for all of the hydroxyl groups to be esterified so long as the kinematic viscosity, water holding percentage and weight-average molecular weight are within the aforementioned ranges.

Examples of (A1) a compound having a chain hydrocarbon moiety and 2-4 hydroxyl groups substituting for hydrogens on the chain hydrocarbon moiety (hereunder also referred to as "compound (A1)") include chain hydrocarbon tetraols, such as alkanetetraols, including pentaerythritol, chain hydrocarbon triols, such as alkanetriols, including glycerins, and chain hydrocarbon diols, such as alkanediols, including glycols.

Examples of (A2) a compound having a chain hydrocarbon moiety and 1 carboxyl group substituting for a hydrogen on the chain hydrocarbon moiety include compounds in which one hydrogen on the hydrocarbon is substituted with one carboxyl group (—COOH), such as fatty acids.

Examples for compound (A) include ($a_1$) an ester of a chain hydrocarbon tetraol and at least one fatty acid, ($a_2$) an ester of a chain hydrocarbon triol and at least one fatty acid, and ($a_3$) an ester of a chain hydrocarbon diol and at least one fatty acid.

[($a_1$) Esters of a Chain Hydrocarbon Tetraol and at Least One Fatty Acid]

Examples of an ester of a chain hydrocarbon tetraol and at least one fatty acid include tetraesters of pentaerythritol and fatty acids, represented by the following formula (1):

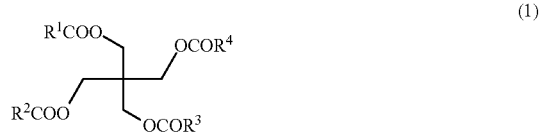

(1)

triesters of pentaerythritol and fatty acids, represented by the following formula (2):

(2)

diesters of pentaerythritol and fatty acids, represented by the following formula (3):

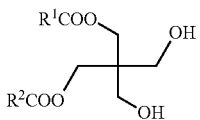
(3)

and monoesters of pentaerythritol and fatty acids, represented by the following formula (4).

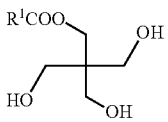
(4)

In the formulas, $R^1$-$R^4$ each represent a chain hydrocarbon.

The fatty acids consisting of the esters of pentaerythritol and fatty acids ($R^1COOH$, $R^2COOH$, $R^3COOH$, and $R^4COOH$) are not particularly restricted so long as the pentaerythritol and fatty acid esters satisfy the conditions for the kinematic viscosity, water holding percentage and weight-average molecular weight, and for example, there may be mentioned saturated fatty acids, such as a $C_2$-$C_{30}$ saturated fatty acids, including acetic acid ($C_2$) ($C_2$ representing the number of carbons, corresponding to the number of carbons of each of $R^1C$, $R^2C$, $R^3C$ or $R^4C$, same hereunder), propanoic acid ($C_3$), butanoic acid ($C_4$) and isomers thereof, such as 2-methylpropanoic acid ($C_4$), pentanoic acid ($C_5$) and isomers thereof, such as 2-methylbutanoic acid ($C_5$) and 2,2-dimethylpropanoic acid ($C_5$), hexanoic acid ($C_6$), heptanoic acid ($C_7$), octanoic acid ($C_8$) and isomers thereof, such as 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid ($C_{26}$), octacosanoic acid ($C_{28}$), triacontanoic acid ($C_{30}$), as well as isomers thereof which are not described above.

The fatty acid may also be an unsaturated fatty acid. Examples of unsaturated fatty acids include $C_3$-$C_{20}$ unsaturated fatty acids, such as monounsaturated fatty acids including crotonic acid ($C_4$), myristoleic acid ($C_{14}$), palmitoleic acid ($C_{16}$), oleic acid ($C_{18}$), elaidic acid ($C_{18}$), vaccenic acid ($C_{18}$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as α-linolenic acid ($C_{18}$) and γ-linolenic acid ($C_{18}$), pinolenic acid ($C_{18}$), eleostearic acids, such as α-eleostearic acid ($C_{18}$) and β-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), and partial hydrogen adducts thereof.

Considering the potential for degradation by oxidation and the like, the ester of pentaerythritol and a fatty acid is preferably an ester of pentaerythritol and a fatty acid, which is derived from a saturated fatty acid, i.e., an ester of pentaerythritol and a saturated fatty acid.

Also, from the viewpoint of lowering the water holding percentage, the ester of pentaerythritol and a fatty acid is preferably a diester, triester or tetraester, more preferably a triester or tetraester, and even more preferably a tetraester.

From the viewpoint of the IOB being from about 0.00 to about 0.60, in a tetraester of pentaerythritol and a fatty acid, the total number of carbons of the fatty acid composing the tetraester of the pentaerythritol and fatty acid, i.e. the total number of carbons of the $R^1C$, $R^2C$, $R^3C$ and $R^4C$ portions in formula (1), is preferably about 15 (the IOB is 0.60 when the total number of carbon atoms is 15).

Examples of tetraesters of pentaerythritol and fatty acids include tetraesters of pentaerythritol with hexanoic acid ($C_6$), heptanoic acid ($C_7$), octanoic acid ($C_8$), such as 2-ethylhexanoic acid ($C_8$), nonanoic acid ($C_9$), decanoic acid ($C_{10}$) and/or dodecanoic acid ($C_{12}$).

From the viewpoint of the IOB being from about 0.00 to about 0.60, in a triester of pentaerythritol and a fatty acid, the total number of carbons of the fatty acid composing the triester of the pentaerythritol and fatty acid, i.e. the total number of carbons of the $R^1C$, $R^2C$ and $R^3C$ portions in formula (2), is preferably about 19 or greater (the IOB is 0.58 when the number of carbon atoms is 19).

From the viewpoint of the IOB being from about 0.00 to about 0.60, in a diester of pentaerythritol and a fatty acid, the total number of carbons of the fatty acid composing the diester of the pentaerythritol and fatty acid, i.e. the total number of carbons of the $R^1C$ and $R^2C$ portion in formula (3), is preferably about 22 or greater (the IOB is 0.59 when the number of carbon atoms is 22).

From the viewpoint of the IOB being from about 0.00 to about 0.60, in a monoester of pentaerythritol and a fatty acid, the total number of carbons of the fatty acid composing the monoester of the pentaerythritol and fatty acid, i.e. the number of carbons of the $R^1C$ portion in formula (4), is preferably about 25 or greater (the IOB is 0.60 when the number of carbon atoms is 25).

The effects of double bonds, triple bonds, iso-branches and tert-branches are not considered in this calculation of the IOB (same hereunder).

Commercial products which are esters of pentaerythritol and fatty acids include UNISTAR H-408BRS and H-2408BRS-22 (mixed product) (both products of NOF Corp.).

[($a_2$) Ester of a Chain Hydrocarbon Triol and at Least One Fatty Acid]

Examples of esters of a chain hydrocarbon triol and at least one fatty acid include triesters of glycerin and fatty acids, represented by formula (5):

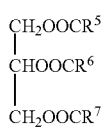
(5)

diesters of glycerin and fatty acids, represented by the following formula (6):

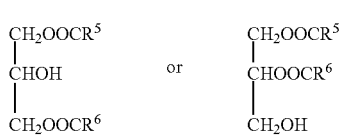
(6)

and monoesters of glycerin and fatty acids, represented by the following formula (7):

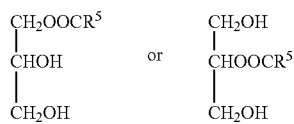  (7)

wherein $R^5$—$R^7$ each represent a chain hydrocarbon.

The fatty acid consisting of the ester of glycerin and a fatty acid ($R^5COOH$, $R^6COOH$ and $R^7COOH$) is not particularly restricted so long as the ester of glycerin and a fatty acid satisfies the conditions for the kinematic viscosity, water holding percentage and weight-average molecular weight, and for example, there may be mentioned the fatty acids mentioned for the "($a_1$) Ester of a chain hydrocarbon tetraol and at least one fatty acid", namely saturated fatty acids and unsaturated fatty acids, and in consideration of the potential for degradation by oxidation and the like, the ester is preferably a glycerin and fatty acid ester, which is derived from a saturated fatty acid, i.e., an ester of glycerin and a saturated fatty acid.

Also, from the viewpoint of lowering the water holding percentage and result in greater hydrophobicity, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or 3 different fatty acids, and mixtures thereof.

Examples of triesters of glycerin and 2 or more fatty acids include triesters of glycerin with octanoic acid ($C_8$) and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_{10}$), dodecanoic acid ($C_{12}$), tetradecanoic acid ($C_{14}$), hexadecanoic acid ($C_{16}$) and octadecanoic acid ($C_{18}$).

In order to obtain a melting point of about 45° C. or less, preferred triesters of glycerin and fatty acids are those with about 40 or less as the total number of carbons of the fatty acid consisting of the triester of glycerin and the fatty acid, i.e., the total number of carbons of the $R^5C$, $R^6C$ and $R^7C$ sections in formula (5).

From the viewpoint of the IOB being from about 0.00 to about 0.60, in a triester of glycerin and a fatty acid, the total number of carbons of the fatty acid composing the triester of the glycerin and fatty acid, i.e. the total number of carbons of the $R^5C$, $R^6C$ and $R^7C$ portions in formula (5), is preferably about 12 or greater (the IOB is 0.60 when the total number of carbon atoms is 12).

Triesters of glycerin and fatty acids, being aliphatic and therefore potential constituent components of the human body, are preferred from the viewpoint of safety.

Commercial products of triesters of glycerin and fatty acids include tri-coconut fatty acid glycerides, NA36, PANACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 or more different fatty acids, and mixtures thereof.

From the viewpoint of the IOB being from about 0.00 to about 0.60, in a diester of glycerin and a fatty acid, the total number of carbons of the fatty acid composing the diester of the glycerin and fatty acid, i.e. the total number of carbons of the $R^5C$ and $R^6C$ portions in formula (6), is preferably about 16 or greater (the IOB is 0.58 when the total number of carbon atoms is 16).

Monoesters of glycerin and fatty acids are also known as monoglycerides, and examples include glycerin and octadecanoic acid ($C_{18}$) monoester, and glycerin and docosanoic acid ($C_{22}$) monoester.

From the viewpoint of the IOB being from about 0.00 to about 0.60, in a monoester of glycerin and a fatty acid, the total number of carbons of the fatty acid composing the monoester of the glycerin and fatty acid, i.e. the number of carbons of the $R^5C$ portion in formula (7), is preferably about 19 or greater (the IOB is 0.59 when the number of carbon atoms is 19).

[($a_3$) Ester of a Chain Hydrocarbon Diol and at Least One Fatty Acid]

Examples of an ester of a chain hydrocarbon diol and at least one fatty acid include monoesters and diesters of fatty acids with $C_2$-$C_6$ chain hydrocarbon diols, such as $C_2$-$C_6$ glycols, including ethylene glycol, propylene glycol, butylene glycol, pentylene glycol and hexylene glycol.

Specifically, examples of an ester of a chain hydrocarbon diol and at least one fatty acid include diesters of $C_2$-$C_6$ glycols and fatty acids, represented by the following formula (8):

  (8)

wherein k represents an integer of 2-6, and $R^8$ and $R^9$ each represent a chain hydrocarbon, and monoesters of $C_2$-$C_6$ glycols and fatty acids, represented by the following formula (9):

  (9)

wherein k represents an integer of 2-6, and $R^8$ is a chain hydrocarbon.

The fatty acid to be esterified in an ester of a $C_2$-$C_6$ glycol and a fatty acid (corresponding to $R^8COOH$ and $R^9COOH$ in formula (8) and formula (9)) is not particularly restricted so long as the ester of the $C_2$-$C_6$ glycol and fatty acid satisfies the conditions for the kinematic viscosity, water holding percentage and weight-average molecular weight, and for example, there may be mentioned the fatty acids mentioned above for the "($a_1$) Ester of a chain hydrocarbon tetraol and at least one fatty acid", namely saturated fatty acids and unsaturated fatty acids, and in consideration of the potential for degradation by oxidation and the like, it is preferably a saturated fatty acid.

From the viewpoint of the IOB being from about 0.00 to about 0.60, in a diester of butylene glycol represented by formula (8) (k=4) and a fatty acid, the total number of carbons of the $R^8C$ and $R^9C$ portions is preferably about 6 or greater (the IOB is 0.60 when the total number of carbon atoms is 6).

From the viewpoint of the IOB being from about 0.00 to about 0.60, in a monoester of ethylene glycol represented by formula (9) (k=2) and a fatty acid, the number of carbons of the $R^8C$ portion is preferably about 12 or greater (the IOB is 0.57 when the number of carbon atoms is 12).

Considering the potential for degradation by oxidation and the like, the ester of the $C_2$-$C_6$ glycol and fatty acid is preferably a $C_2$-$C_6$ glycol and fatty acid ester derived from a saturated fatty acid, or in other words, an ester of a $C_2$-$C_6$ glycol and a saturated fatty acid.

Also, from the viewpoint of lowering the water holding percentage, the ester of the $C_2$-$C_6$ glycol and fatty acid is preferably a glycol and fatty acid ester derived from a glycol with a greater number of carbons, such as an ester of a glycol and a fatty acid derived from butylene glycol, pentylene glycol or hexylene glycol.

Also, from the viewpoint of lowering the water holding percentage, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of (B1) a compound having a chain hydrocarbon moiety and 2-4 hydroxyl groups substituting for hydrogens on the chain hydrocarbon moiety and (B2) a compound having a chain hydrocarbon moiety and 1 hydroxyl group substituting for a hydrogen on the chain hydrocarbon moiety]

In the (B) ether of (B1) a compound having a chain hydrocarbon moiety and 2-4 hydroxyl groups substituting for hydrogens on the chain hydrocarbon moiety and (B2) a compound having a chain hydrocarbon moiety and 1 hydroxyl group substituting for a hydrogen on the chain hydrocarbon moiety (hereunder also referred to as "compound (B)"), it is not necessary for all of the hydroxyl groups to be etherified so long as the kinematic viscosity, water holding percentage and weight-average molecular weight are within the aforementioned ranges.

Examples of (B1) a compound having a chain hydrocarbon moiety and 2-4 hydroxyl groups substituting for hydrogens on the chain hydrocarbon moiety (hereunder also referred to as "compound (B1)") include those mentioned for "compound (A)" as compound (A1), such as pentaerythritol, glycerin and glycol.

Examples of (B2) a compound having a chain hydrocarbon moiety and 1 hydroxyl group substituting for a hydrogen on the chain hydrocarbon moiety (hereunder also referred to as "compound (B2)") include compounds wherein 1 hydrogen on the hydrocarbon is substituted with 1 hydroxyl group (—OH), such as aliphatic monohydric alcohols, including saturated aliphatic monohydric alcohols and unsaturated aliphatic monohydric alcohols.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$) and isomers thereof, including isopropyl alcohol ($C_3$), butyl alcohol ($C_4$) and isomers thereof, including sec-butyl alcohol ($C_4$) and tert-butyl alcohol ($C_4$), pentyl alcohol ($C_5$), hexyl alcohol ($C_6$), heptyl alcohol ($C_7$), octyl alcohol ($C_8$) and isomers thereof, including 2-ethylhexyl alcohol ($C_8$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers other than those mentioned.

Unsaturated aliphatic monohydric alcohols include those wherein 1 C—C single bond of a saturated aliphatic monohydric alcohol mentioned above is replaced with a C=C double bond, such as oleyl alcohol, and for example, such alcohols are commercially available by New Japan Chemical Co., Ltd. as the RIKACOL Series and UNJECOL Series.

Examples for compound (B) include ($b_1$) an ether of a chain hydrocarbon tetraol and at least one aliphatic monohydric alcohol, such as monoethers, diethers, triethers and tetraethers, preferably diethers, triethers and tetraethers, more preferably triethers and tetraethers and even more preferably tetraethers, ($b_2$) an ether of a chain hydrocarbon triol and at least one aliphatic monohydric alcohol, such as monoethers, diethers and triethers, preferably diethers and triethers and more preferably triethers, and ($b_3$) an ether of a chain hydrocarbon diol and at least one aliphatic monohydric alcohol, such as monoethers and diethers, and preferably diethers.

Examples of an ether of a chain hydrocarbon tetraol and at least one aliphatic monohydric alcohol include tetraethers, triethers, diethers and monoethers of pentaerythritol and aliphatic monohydric alcohols, represented by the following formulas (10)-(13):

(10)

(11)

(12)

(13)

wherein $R^{10}$-$R^{13}$ each represent a chain hydrocarbon.

Examples of an ether of a chain hydrocarbon triol and at least one aliphatic monohydric alcohol include triethers, diethers and monoethers of glycerin and aliphatic monohydric alcohols, represented by the following formulas (14)-(16):

(14)

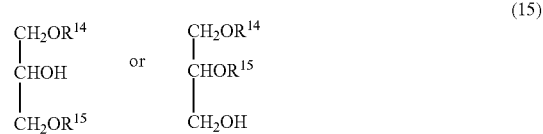

(15)

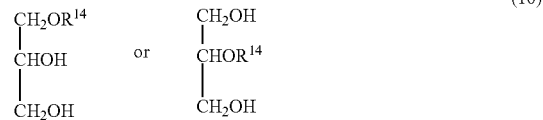

(16)

wherein $R^{14}$-$R^{16}$ each represent a chain hydrocarbon.

Examples of an ether of a chain hydrocarbon diol and at least one aliphatic monohydric alcohol include diethers of $C_2$-$C_6$ glycols and aliphatic monohydric alcohols, represented by the following formula (17):

$$R^{17}OC_{10}H_{2n}OR^{18} \qquad (17)$$

wherein n is an integer of 2-6, and $R^{17}$ and $R^{18}$ are each a chain hydrocarbon, and monoethers of $C_2$-$C_6$ glycols and aliphatic monohydric alcohols, represented by the following formula (18):

$$R^{17}OC_nH_{2n}OH \qquad (18)$$

wherein n is an integer of 2-6, and $R^{17}$ is a chain hydrocarbon.

From the viewpoint of the IOB being between about 0.00 and about 0.60, in a tetraether of pentaerythritol and an aliphatic monohydric alcohol, the total number of carbon atoms of the aliphatic monohydric alcohol composing the tetraether of pentaerythritol and the aliphatic monohydric alcohol, i.e. the total number of carbon atoms of the $R^{10}$, $R^{11}$, $R^{12}$ and $R^{13}$ portions in formula (10), is preferably about 4 or greater (the IOB is 0.44 when the total number of carbon atoms is 4).

From the viewpoint of the IOB being between about 0.00 and about 0.60, in a triether of pentaerythritol and an aliphatic monohydric alcohol, the total number of carbon atoms of the aliphatic monohydric alcohol composing the triether of pentaerythritol and the aliphatic monohydric alcohol, i.e. the total number of carbon atoms of the $R^{10}$, $R^{11}$ and $R^{12}$ portions in formula (11), is preferably about 9 or greater (the IOB is 0.57 when the total number of carbon atoms is 9).

From the viewpoint of the IOB being between about 0.00 and about 0.60, in a diether of pentaerythritol and an aliphatic monohydric alcohol, the total number of carbon atoms of the aliphatic monohydric alcohol composing the diether of pentaerythritol and the aliphatic monohydric alcohol, i.e. the total number of carbon atoms of the $R^{10}$ and $R^{11}$ portions in formula (12), is preferably about 15 or greater (the IOB is 0.60 when the total number of carbon atoms is 15).

From the viewpoint of the IOB being between about 0.00 and about 0.60, in a monoether of pentaerythritol and an aliphatic monohydric alcohol, the number of carbon atoms of the aliphatic monohydric alcohol composing the monoether of pentaerythritol and the aliphatic monohydric alcohol, i.e. the number of carbon atoms of the $R^{10}$ portion in formula (13), is preferably about 22 or greater (the IOB is 0.59 when the number of carbon atoms is 22).

From the viewpoint of the IOB being between about 0.00 and about 0.60, in a triether of glycerin and an aliphatic monohydric alcohol, the total number of carbon atoms of the aliphatic monohydric alcohol composing the triether of glycerin and the aliphatic monohydric alcohol, i.e. the total number of carbon atoms of the $R^{14}$, $R^{15}$ and $R^{16}$ portions in formula (14), is preferably about 3 or greater (the IOB is 0.50 when the total number of carbon atoms is 3).

From the viewpoint of the IOB being between about 0.00 and about 0.60, in a diether of glycerin and an aliphatic monohydric alcohol, the total number of carbon atoms of the aliphatic monohydric alcohol composing the diether of glycerin and the aliphatic monohydric alcohol, i.e. the total number of carbon atoms of the $R^{14}$ and $R^{15}$ portions in formula (15), is preferably about 9 or greater (the IOB is 0.58 when the total number of carbon atoms is 9).

From the viewpoint of the IOB being between about 0.00 and about 0.60, in a monoether of glycerin and an aliphatic monohydric alcohol, the number of carbon atoms of the aliphatic monohydric alcohol composing the monoether of glycerin and the aliphatic monohydric alcohol, i.e. the number of carbon atoms of the $R^{14}$ portion in formula (16), is preferably 16 or greater (the IOB is 0.58 when the number of carbon atoms is 16).

From the viewpoint of the IOB being from about 0.00 to about 0.60, in a diether of butylene glycol represented by formula (17) (n=4) and an aliphatic monohydric alcohol, the total number of carbon atoms of the $R^{17}$ and $R^{18}$ portions is preferably about 2 or greater (the IOB is 0.33 when the total number of carbon atoms is 2).

From the viewpoint of the IOB being from about 0.00 to about 0.60, in a monoether of ethylene glycol represented by formula (18) (n=2) and an aliphatic monohydric alcohol, the number of carbon atoms of the $R^{17}$ portion is preferably about 8 or greater (the IOB is 0.60 when the number of carbon atoms is 8).

Compound (B) may be produced by dehydrating condensation of compound (B1) and compound (B2) in the presence of an acid catalyst.

[(C) Ester of (C1) a carboxylic acid, hydroxy acid, alkoxy acid or oxoacid comprising a chain hydrocarbon moiety and 2-4 carboxyl groups substituting for hydrogens on the chain hydrocarbon moiety and (C2) a compound having a chain hydrocarbon moiety and 1 hydroxyl group substituting for a hydrogen on the chain hydrocarbon moiety]

In the (C) ester of (C1) a carboxylic acid, hydroxy acid, alkoxy acid or oxoacid comprising a chain hydrocarbon moiety and 2-4 carboxyl groups substituting for hydrogens on the chain hydrocarbon moiety and (C2) a compound having a chain hydrocarbon moiety and 1 hydroxyl group substituting for a hydrogen on the chain hydrocarbon moiety (hereunder also referred to as "compound (C)"), it is not necessary for all of the carboxyl groups to be esterified so long as the kinematic viscosity, water holding percentage and weight-average molecular weight are within the aforementioned ranges.

Examples of (C1) a carboxylic acid, hydroxy acid, alkoxy acid or oxoacid comprising a chain hydrocarbon moiety and 2-4 carboxyl groups substituting for hydrogens on the chain hydrocarbon moiety (hereunder also referred to as "compound (C1)") include chain hydrocarbon carboxylic acids with 2-4 carboxyl groups, such as chain hydrocarbon dicarboxylic acids including alkanedicarboxylic acids, such as ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, including alkanetricarboxylic acids, such as propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, including alkanetetracarboxylic acids, such as butanetetraoic acid, pentanetetraoic acid, hexanetetraoic acid, heptanetetraoic acid, octanetetraoic acid, nonanetetraoic acid and decanetetraoic acid.

Compound (C1) includes chain hydrocarbon hydroxy acids with 2-4 carboxyl groups, such as malic acid, tartaric acid, citric acid and isocitric acid, chain hydrocarbon alkoxy acids with 2-4 carboxyl groups, such as O-acetylcitric acid, and chain hydrocarbon oxoacids with 2-4 carboxyl groups.

(C2) Compound having a chain hydrocarbon moiety and 1 hydroxyl group substituting for a hydrogen on the chain hydrocarbon moiety includes those mentioned for "compound (B)", such as aliphatic monohydric alcohols.

Compound (C) may be ($c_1$) an ester, for example a monoester, diester, triester or tetraester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and at least one aliphatic monohydric alcohol, ($c_2$) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and at least one aliphatic monohydric alcohol, or ($c_3$) an ester, for example, a monoester or diester, and preferably a diester, of a chain hydrocarbon dicarboxylic acid, hydroxy acid, alkoxy acid or oxoacid with 2 carboxyl groups, and at least one aliphatic monohydric alcohol.

Examples for compound (C) include dioctyl adipate, and tributyl 0-acetylcitrate, of which commercially available products exist.

[(D) Compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety]

The (D) compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety (hereunder also referred to as "compound (D)") may be ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, or ($d_4$) a dialkyl carbonate.

[($d_1$) Ether of an Aliphatic Monohydric Alcohol and an Aliphatic Monohydric Alcohol]

Ethers of an aliphatic monohydric alcohol and an aliphatic monohydric alcohol include compounds having the following formula (19):

$$R^{19}OR^{20} \qquad (19)$$

wherein $R^{19}$ and $R^{20}$ each represent a chain hydrocarbon.

The aliphatic monohydric alcohol consisting of the ether (corresponding to $R^{19}OH$ and $R^{20}OH$ in formula (19)) is not particularly restricted so long as the ether satisfies the conditions for the kinematic viscosity, water holding percentage and weight-average molecular weight, and for example, it may be one of the aliphatic monohydric alcohols mentioned for "compound (B)".

[($d_2$) Dialkyl Ketone]

The dialkyl ketone may be a compound of the following formula (20):

$$R^{21}COR^{22} \qquad (20)$$

wherein $R^{21}$ and $R^{22}$ are each an alkyl group.

The dialkyl ketone may be a commercially available product, or it may be obtained by a known method, such as by oxidation of a secondary alcohol with chromic acid or the like.

[($d_3$) Ester of a Fatty Acid and an Aliphatic Monohydric Alcohol]

Examples of esters of a fatty acid and an aliphatic monohydric alcohol include compounds having the following formula (21):

$$R^{23}COOR^{24} \qquad (21)$$

wherein $R^{23}$ and $R^{24}$ each represent a chain hydrocarbon.

Examples of fatty acids consisting of these esters (corresponding to $R^{23}COOH$ in formula (21)) include the fatty acids mentioned for the "($a_1$) an ester of a chain hydrocarbon tetraol and at least one fatty acids", and specifically these include saturated fatty acids and unsaturated fatty acids, with saturated fatty acids being preferred in consideration of the potential for degradation by oxidation and the like. The aliphatic monohydric alcohol consisting of the ester (corresponding to $R^{24}OH$ in formula (21)) may be one of the aliphatic monohydric alcohols mentioned for "compound (B)".

Examples of esters of such fatty acids and aliphatic monohydric alcohols include esters of dodecanoic acid ($C_{12}$) and dodecyl alcohol ($C_{12}$) and esters of tetradecanoic acid ($C_{14}$) and dodecyl alcohol ($C_{12}$), and examples of commercial products of esters of such fatty acids and aliphatic monohydric alcohols include ELECTOL WE20 and ELECTOL WE40 (both products of NOF Corp.).

[($d_4$) Dialkyl Carbonate]

The dialkyl carbonate may be a compound of the following formula (22):

$$R^{25}OC(=O)OR^{26} \qquad (22)$$

wherein $R^{25}$ and $R^{26}$ are each an alkyl group.

The dialkyl carbonate may be a commercially available product, or it may be synthesized by reaction between phosgene and an alcohol, reaction between formic chloride and an alcohol or alcoholate, or reaction between silver carbonate and an alkyl iodide.

From the viewpoint of the water holding percentage and vapor pressure, the weight-average molecular weight is preferably about 100 or greater and more preferably about 200 or greater, for ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, and ($d_4$) a dialkyl carbonate.

If the total number of carbon atoms is about 8 in a ($d_2$) dialkyl ketone, the melting point will be approximately −50° C. and the vapor pressure will be about 230 Pa at 20° C., in the case of 5-nonanone, for example.

[(E) Polyoxy $C_3$-$C_6$ alkylene glycol, or alkyl ester or alkyl ether thereof]

The (E) polyoxy $C_3$-$C_6$ alkylene glycol, or alkyl ester or alkyl ether thereof (hereunder also referred to as "compound (E)") may be ($e_1$) a polyoxy $C_3$-$C_6$ alkylene glycol, ($e_2$) an ester of a polyoxy $C_3$-$C_6$ alkylene glycol and at least one fatty acid, or ($e_3$) an ether of a polyoxy $C_3$-$C_6$ alkylene glycol and at least one aliphatic monohydric alcohol. These will now be explained.

[($e_1$) Polyoxy $C_3$-$C_6$ Alkylene Glycol]

Polyoxy $C_3$-$C_6$ alkylene glycols refer to i) homopolymers having one unit selected from the group consisting of oxy $C_3$-$C_6$ alkylene units, such as oxypropylene unit, oxybutylene unit, oxypentylene unit and oxyhexylene unit and having hydroxyl groups at both ends, ii) block copolymers having 2 or more units selected from oxy $C_3$-$C_6$ alkylene units described above and oxyhexylene unit and having hydroxyl groups at both ends, or iii) random copolymers having 2 or more units selected from oxy $C_3$-$C_6$ alkylene units described above and having hydroxyl groups at both ends.

The polyoxy $C_3$-$C_6$ alkylene glycol can be represented by the following formula (23):

$$HO\text{---}(C_mH_{2m}O)_n\text{---}H \qquad (23)$$

wherein m represents an integer of 3-6.

The present inventors have found that with polypropylene glycol (corresponding to a homopolymer of formula (23) where m=3), the condition for the water holding percentage is not satisfied when the weight-average molecular weight is less than about 1,000. Therefore, polypropylene glycol homopolymer is not included in the scope of the blood slipping agent described above, and propylene glycol should be included in the ($e_1$) polyoxy $C_3$-$C_6$ alkylene glycol only as a copolymer or random polymer with another glycol.

Incidentally, investigation by the present inventors suggests that with polyethylene glycol (corresponding to a homopolymer of formula (23) where m=2), the condition for the kinematic viscosity and water holding percentage cannot be satisfied when the weight-average molecular weight is less than about 1,000.

From the viewpoint of the IOB being about 0.00 to about 0.60, when formula (23) is polybutylene glycol (a homopolymer where m=4), for example, preferably n≥about 7 (when n=7, the IOB is 0.57).

Examples of commercial products of poly $C_3$-$C_6$ alkylene glycols include UNIOL™ PB-500 and PB-700 (all products of NOF Corp.).

[($e_2$) Ester of a Polyoxy $C_3$-$C_6$ Alkylene Glycol and at Least One Fatty Acid]

Examples of an ester of a polyoxy $C_3$-$C_6$ alkylene glycol and at least one fatty acids include the polyoxy $C_3$-$C_6$ alkylene glycols mentioned for "($e_1$) Polyoxy $C_3$-$C_6$ alkylene glycol" in which one or both OH ends have been esterified with fatty acids, i.e. monoesters and diesters.

Examples of fatty acids to be esterified in the ester of a polyoxy $C_3$-$C_6$ alkylene glycol and at least one fatty acid include the fatty acids mentioned for the "($a_1$) Ester of a chain hydrocarbon tetraol and at least one fatty acid", and specifically these include saturated fatty acids and unsaturated fatty acids, with saturated fatty acids being preferred in consideration of the potential for degradation by oxidation and the like.

[($e_3$) Ether of a Polyoxy $C_3$-$C_6$ Alkylene Glycol and at Least One Aliphatic Monohydric Alcohol]

Examples of an ether of a polyoxy $C_3$-$C_6$ alkylene glycols and at least one aliphatic monohydric alcohol include the polyoxy $C_3$-$C_6$ alkylene glycols mentioned for "($e_1$) Polyoxy $C_3$-$C_6$ alkylene glycol" wherein one or both OH ends have been etherified by an aliphatic monohydric alcohol, i.e. monoethers and diethers.

In an ether of a polyoxy $C_3$-$C_6$ alkylene glycol and at least one aliphatic monohydric alcohol, the aliphatic monohydric alcohol to be etherified may be an aliphatic monohydric alcohol among those mentioned for "compound (B)".

[(F) Chain Hydrocarbon]

Examples of chain hydrocarbons include ($f_1$) chain alkanes, such as straight-chain alkanes and branched chain alkanes. Straight-chain alkanes with melting points of about 45° C. or less have up to about 22 carbon atoms, and at a vapor pressure of 1 atmosphere and no greater than about 0.01 Pa at 25° C., the number of carbon atoms is 13 or greater. Branched chain alkanes tend to have lower melting points than chain alkanes, given the same number of carbon atoms. Branched chain alkanes may therefore include those with 22 and more carbon atoms, even with melting points of below about 45° C.

Examples of commercially available hydrocarbon products include PARLEAM 6 (NOF Corp.).

In an absorbent article according to one embodiment of this disclosure, the blood slipping agent-containing first region and the blood slipping agent-containing second regions contain the aforementioned blood slipping agent.

In an absorbent article according to another embodiment of this disclosure, the blood slipping agent-containing first region and/or blood slipping agent-containing second regions consist entirely of the aforementioned blood slipping agent. Stated differently, the top sheet has a blood slipping agent-containing first region and/or blood slipping agent-containing second regions consisting entirely of a blood slipping agent, in the excretory opening contact region.

In an absorbent article according to another embodiment of this disclosure, the blood slipping agent-containing first region and/or blood slipping agent-containing second regions comprise a blood slipping agent-containing composition including the aforementioned blood slipping agent and at least one other component. Stated differently, in an absorbent article according to another embodiment of this disclosure, the top sheet has, in the excretory opening contact region, a blood slipping agent-containing first region and/or a blood slipping agent-containing second regions comprising a blood slipping agent-containing composition including the aforementioned blood slipping agent and at least one other component.

Such a blood slipping agent-containing composition will now be described.

[Blood Slipping Agent-Containing Composition]

The blood slipping agent-containing composition contains a blood slipping agent and at least one other component. The other component is not particularly restricted so long as it does not inhibit the effect of the present disclosure, and it may be any one commonly employed in absorbent articles of the art, and especially top sheets.

Examples for the other component(s) include silicone oils, silicones, silicone-based resins and the like.

Examples for the other component(s) also include antioxidants, such as BHT (2,6-di-t-butyl-p-cresol), BHA (butylated hydroxyanisole) and propyl gallate.

Further examples for the other component(s) include vitamins, such as natural vitamins and synthetic vitamins. Examples of vitamins include water-soluble vitamins, such as group B vitamins, including vitamin $B_1$, vitamin $B_2$, vitamin $B_3$, vitamin $B_5$, vitamin $B_6$, vitamin $B_7$, vitamin $B_9$ and vitamin $B_{12}$, and vitamin C.

Other examples of vitamins include fat-soluble vitamins, such as group A vitamins, group D vitamins, group E vitamins and group K vitamins.

The derivatives of these vitamins are also included.

Examples for the other component(s) include amino acids, such as alanine, arginine, lysine, histidine, proline and hydroxyproline, and peptides.

Other examples for the other component(s) include zeolite, such as natural zeolite, examples of which include analcite, chabazite, heulandite, natrolite, stilbite and thomosonite, and synthetic zeolite.

Still other examples for the other component(s) include cholesterol, hyaluronic acid, lecithin and ceramide.

Yet other examples for the other component(s) include drugs, such as skin astringents, anti-pimple medications, anti-wrinkle agents, anti-cellulite agents, skin whiteners, antimicrobial agents and antifungal agents.

Examples of skin astringents include zinc oxide, aluminum sulfate, tannic acid and the like, and oil-soluble skin astringents, such as fat-soluble polyphenols. Fat-soluble polyphenols include natural fat-soluble polyphenols, such as barley extract, otogiriso extract, white deadnettle extract, chamomilla extract, burdock extract, *salvia* extract, linden extract, common lime extract, white birch extract, common horsetail extract, sage extract, *salvia* extract, walnut (*J. regia* L. var. *orientalis*) extract, hibiscus extract, loquat leaf extract, Miquel's linden extract, hop extract, common horse-chestnut extract and *coix* seed extract.

Examples of anti-pimple medications include salicylic acid, benzoyl peroxide, resorcinol, sulfur, erythromycin and zinc.

Examples of anti-wrinkle agents include lactic acid, salicylic acid, salicylic acid derivatives, glycolic acid, phytic acid, lipoic acid and lysophosphatidic acid.

Examples of anti-cellulite agents include xanthine compounds, such as aminophylline, caffeine, theophylline and theobromine.

Examples of skin whiteners include niacinamide, kojic acid, arbutin, glucosamine and its derivatives, phytosterol derivatives, and ascorbic acid and its derivatives, as well as mulberry extract and placenta extract.

Examples for the other component(s) also include anti-inflammatory components, pH regulators, antimicrobial agents, humectants, aromatics, pigments, dyes, pigments and plant extracts. Examples of anti-inflammatory components include naturally-derived anti-inflammatory drugs, such as peony, golden grass, otogiriso, chamomile, licorice, peach leaf, Japanese mugwort and *perilla* extract, and synthetic anti-inflammatory drugs, such as allantoin and dipotassium glycyrrhizinate.

Examples of pH regulators include those that keep the skin weakly acidic, such as malic acid, succinic acid, citric acid, tartaric acid and lactic acid.

Titanium oxide is an example of a pigment.

The blood slipping agent-containing composition contains the blood slipping agent and the one or more other components at preferably about 50 to about 99 mass % and about 1 to about 50 mass %, respectively, more preferably about 60 to about 99 mass % and about 1 to about 40 mass %, respectively, even more preferably about 70 to about 99 mass % and about 1 to about 30 mass %, respectively, yet more preferably about 80 to about 99 mass % and about 1 to about 20 mass %, respectively, even yet more preferably about 90 to 99 mass % and about 1 to about 10 mass %, respectively, and even yet more preferably about 95 to 99 mass % and about 1 to about 5 mass %, respectively. These ranges are from the viewpoint of the effect of the present disclosure.

The blood slipping agent-containing composition preferably contains a surfactant in no greater than the amount from hydrophilicizing treatment of the top sheet or second sheet. More specifically, the blood slipping agent-containing composition contains a surfactant in a basis weight range of preferably about 0.0 to about 1.0 g/m$^2$, more preferably about 0.0 to about 0.8 g/m$^2$, even more preferably about 0.1 to about 0.5 g/m$^2$, and yet more preferably about 0.1 to about 0.3 g/m$^2$.

This is because when the amount of surfactant is increased, menstrual blood will tend to be retained in the top sheet. The surfactant, incidentally, has no water holding percentage. This is because there is no layer of the substance to be measured, due to admixture with water.

The blood slipping agent-containing composition contains water in a basis weight range of preferably about 0.0 to about 1.0 g/m$^2$, more preferably about 0.0 to about 0.8 g/m$^2$, even more preferably about 0.1 to about 0.5 g/m$^2$, and yet more preferably about 0.1 to about 0.3 g/m$^2$.

Since water lowers the absorption performance of the absorbent article, the amount is preferably low.

Similar to the blood slipping agent, the blood slipping agent-containing composition, as a composition, has at 40° C., a kinematic viscosity of preferably about 0 to about 80 mm$^2$/s, more preferably a kinematic viscosity of about 1 to about 70 mm$^2$/s, even more preferably a kinematic viscosity of about 3 to about 60 mm$^2$/s, yet more preferably a kinematic viscosity of about 5 to about 50 mm$^2$/s, and even yet more preferably a kinematic viscosity of about 7 to about 45 mm$^2$/s.

If the kinematic viscosity of the blood slipping agent-containing composition exceeds 80 mm$^2$/s, the viscosity will increase, and the blood slipping agent composition may not slide down into the interior of the absorbent article as easily with menstrual blood that has reached the skin contact surface of the top sheet.

When the blood slipping agent-containing composition contains a component that is miscible with the blood slipping agent, as at least one other component, the other component preferably has a weight-average molecular weight of less than about 1000, and more preferably a weight-average molecular weight of less than about 900. This is because, if the weight-average molecular weight is about 1000 or higher, tack may result in the blood slipping agent-containing composition itself, tending to create a feeling of unpleasantness for the wearer. If the weight-average molecular weight increases, the viscosity of the blood slipping agent-containing composition will tend to increase, and it will therefore be difficult to lower the viscosity of the blood slipping agent composition by heating to a viscosity suitable for coating, and as a result, the blood slipping agent may need to be diluted with a solvent.

The blood slipping agent-containing composition, as a composition, has a water holding percentage of about 0.01 to about 4.0 mass %, preferably it has a water holding percentage of about 0.02 to about 3.5 mass %, more preferably it has a water holding percentage of about 0.03 to about 3.0 mass %, even more preferably it has a water holding percentage of about 0.04 to about 2.5 mass %, and yet more preferably it has a water holding percentage of about 0.05 to about 2.0 mass %.

A low water holding percentage value will tend to lower the affinity between the blood slipping agent composition and menstrual blood, thus inhibiting it from sliding down into the interior of the absorbent article with menstrual blood that has reached the skin contact surface of the top sheet.

When the blood slipping agent-containing composition contains solid matter, it is preferably removed by filtration for measurement of the kinematic viscosity and water holding percentage.

[Method for Producing Absorbent Article]

In a method for producing an absorbent article according to one embodiment of this disclosure, after an absorbent article has been produced by a method known in the technical field, the blood slipping agent or blood slipping agent-containing composition is coated in at least the excretory opening contact region of the top sheet to form a blood slipping agent-containing first region, and by coating the same or a different blood slipping agent or blood slipping agent-containing composition as that used to form the blood slipping agent-containing first region, it is possible to form blood slipping agent-containing second regions on the pair of flaps.

In a method for producing an absorbent article according to another embodiment of this disclosure, a blood slipping agent-containing first region on the top sheet may be formed by coating a blood slipping agent or blood slipping agent-containing composition onto at least the excretory opening contact region of the top sheet, the same or a different blood slipping agent or blood slipping agent-containing composition as the one used to form the blood slipping agent-containing first region may be coated on the pair of side flaps to form blood slipping agent-containing second regions on the side flaps, and the same or a different blood slipping agent or blood slipping agent-containing composition as the one used to form the blood slipping agent-containing first region and/or blood slipping agent-containing second regions may be coated on the pair of hip flaps to form blood slipping agent-containing second regions on the hip flaps.

In an embodiment in which the absorbent article is an individually packaged absorbent article, the absorbent article may subsequently be triple-folded, quadruple-folded, etc. and individually packaged to produce an individually packaged absorbent article.

The blood slipping agent or blood slipping agent-containing composition may, if desired, be applied as a coating solution containing a volatile solvent, such as an alcohol-based solvent, ester-based solvent or aromatic solvent. If the coating solution includes a volatile solvent, the viscosity of the coating solution containing the blood slipping agent or blood slipping agent-containing composition will be lowered, thereby allowing the application steps to be simplified, facilitating application and making heating during application unnecessary.

There are no particular restrictions on the method of applying the blood slipping agent or blood slipping agent-containing composition, or the coating solution containing it, and if necessary the blood slipping agent or blood slipping agent-containing composition or the coating solution containing it may be heated, and a coating applicator, for example a non-contact coater, such as a spiral coater, curtain coater, spray coater or dip coater, or a contact coater, may be used for application of the blood slipping agent or blood slipping agent-containing composition or the coating solution containing it. The coating applicator is preferably a non-contact coater, from the viewpoint of uniformly dispersing the droplet or particulate modifying agent throughout, and from the viewpoint of not causing damage in the material.

The blood slipping agent or blood slipping agent-containing composition, or the coating solution containing it, may be coated directly, if it is a liquid at room temperature, or it may be heated to lower the viscosity, and when it is a solid at room temperature, it may be heated to liquefaction and coated from a control seam HMA (Hot Melt Adhesive) gun. By increasing the air pressure of the control seam HMA gun, it is possible to apply the blood slipping agent or blood slipping agent-containing composition as fine particulates.

The coating amount of the blood modifying agent or blood slipping agent-containing composition can be adjusted, for example, by adjusting the discharged amount from a control seam HMA gun.

In a production method according to one embodiment of this disclosure, an absorbent body, back sheet, side sheet and the like may be combined to produce an absorbent article after the blood slipping agent or blood slipping agent-containing composition has been coated onto the top sheet or pair of flaps, while in a production method according to another embodiment of this disclosure, the blood slipping agent or blood slipping agent-containing composition may be coated onto the top sheet or the pair of flaps after the absorbent article has been formed from a top sheet, absorbent body, back sheet and the like.

From the viewpoint of minimizing equipment investment, the blood slipping agent or blood slipping agent-containing composition is preferably coated on the top sheet or the pair of flaps during a step of the manufacturing line for the absorbent article, and in order to prevent shedding of the blood slipping agent or blood slipping agent-containing composition which may contaminate the line, the blood slipping agent or blood slipping agent-containing composition is preferably coated onto the top sheet or the pair of flaps during a downstream step of the manufacturing line.

In a method for producing an absorbent article according to another embodiment of this disclosure, a portion of the blood slipping agent of the top sheet, or a portion of the blood slipping agent or blood slipping agent-containing composition of the top sheet, may be transferred to two flaps to form blood slipping agent-containing second regions on the flaps.

Utilizing transfer, it is possible to omit the apparatus and step for coating of the blood slipping agent or blood slipping agent-containing composition on the flaps, and to thus simplify the apparatus and process.

Figure 3:
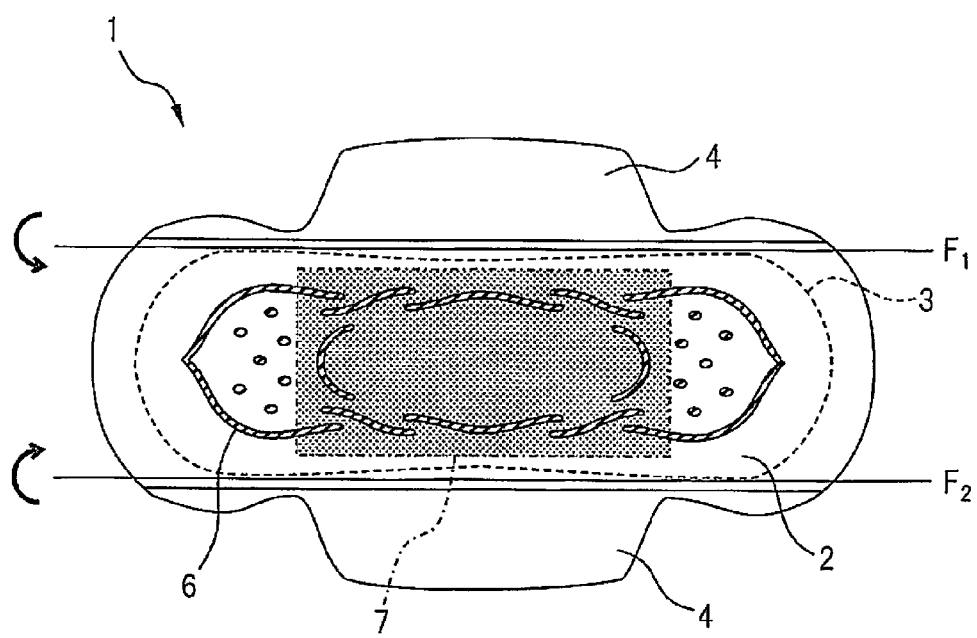
FIG. 3 is a diagram illustrating an example of production steps for the absorbent article 1 shown in FIG. 1.

FIG. 3 is a diagram illustrating an example of production steps for the absorbent article 1 shown in FIG. 1.

The absorbent article shown in FIG. 3 is the same as the absorbent article 1 shown in FIG. 1, except that the pair of side flaps 4 do not include blood slipping agent-containing second regions 8. In FIG. 3, the side sheets are omitted for clarity of illustration.

An absorbent article 1 is prepared in which the top sheet 2 contains the blood slipping agent to be transferred to the pair of flaps 4, as shown in FIG. 3. More specifically, in the absorbent article 1 shown in FIG. 3, the excretory opening contact region of the top sheet 2 has a blood slipping agent-containing first region 7 containing the blood slipping agent to be transferred to the pair of flaps 4. In consideration of transfer of a portion of the blood slipping agent, the blood slipping agent-containing first region 7 may be adjusted so as to contain a blood slipping agent with a greater basis weight than the final basis weight of the blood slipping agent.

Next, the two side flaps 4 are folded over onto the top sheet 2, and more specifically onto the blood slipping agent-containing first region 7 of the top sheet 2, along the axes $F_1$ and $F_2$ that are essentially parallel in the lengthwise direction of the absorbent article 1, as indicated by the arrow in FIG. 3.

Figure 4:
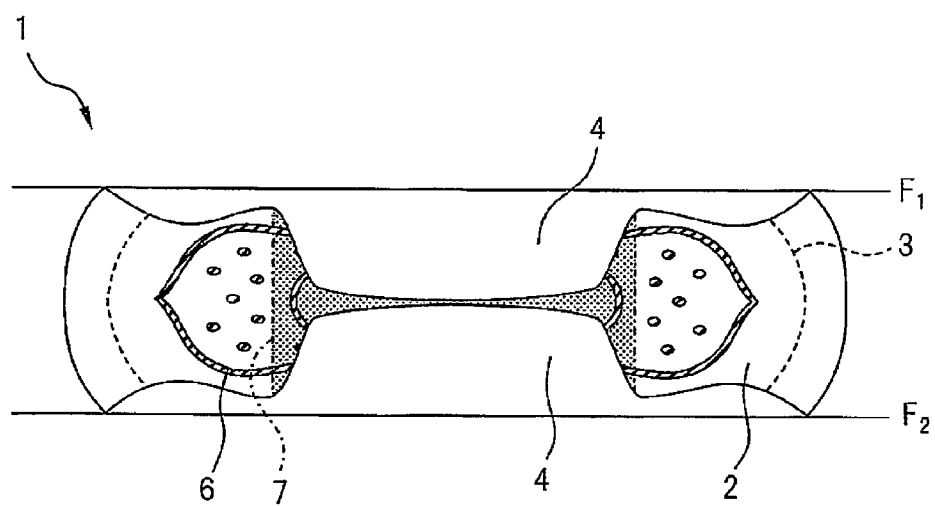
FIG. 4 is a diagram showing the absorbent article 1 in a state where side flaps 4 are folded over onto the top sheet 2 along folding axes $F_1$ and $F_2$.

FIG. 4 is a diagram showing the absorbent article 1 in a state where side flaps 4 are folded over onto the top sheet 2 along folding axes $F_1$ and $F_2$. After folding over the side flaps 4 onto the top sheet 2, a portion of the blood slipping agent of the top sheet 2, and more specifically a portion of the blood slipping agent in the blood slipping agent-containing first region 7 of the top sheet 2, may be allowed to migrate to the facing sections of the side flaps 4 to form blood slipping agent-containing second regions 8.

The absorbent article 1 shown in FIG. 4 is the same as the absorbent article 1 shown in FIG. 1 when the pair of side flaps 4 are reopened along the axes $F_1$ and $F_2$.

In order to transfer the blood slipping agent, the top sheet and the two side flaps may be actively pressed for bonding after folding along the axes $F_1$ and $F_2$, but the pressing can be omitted if the absorbent article is to be sold as an individually packaged product after folding in a triple-fold or quadruple-fold manner along a plurality of folding axes that are essentially perpendicular to the lengthwise direction of the absorbent article, and individually packaged. This is because the pressure applied during transport and storage of the absorbent article will allow the blood slipping agent of the top sheet to migrate into the two side flaps.

Figure 5:
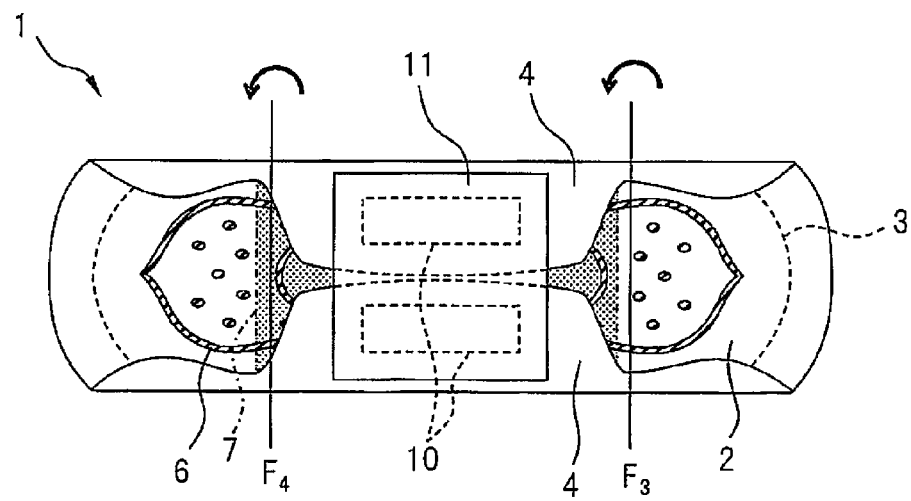
FIG. 5 is a diagram illustrating an example of an individual package of the absorbent article 1 shown in FIG. 4.

FIG. 5 is a diagram illustrating an example of an individual package of the absorbent article 1 shown in FIG. 4. The absorbent article 1 shown in FIG. 5 is formed by attaching an adhesive section 10, for anchoring the absorbent article 1 to the clothing of the wearer, and a release sheet 11, to the surface of the clothing side sheet of the pair of side flaps 4 of the absorbent article 1 shown in FIG. 4. Next, the absorbent article 1 is folded along the folding axis $F_3$ so that the top sheet 2 is facing the inner side, as indicated by the right arrow in FIG. 5, and the absorbent article 1 is folded along the folding axis $F_4$ so that the top sheet 2 is facing the inner side, as indicated by the left arrow in FIG. 5, and it is individually packaged to produce a triple-folded individually packaged absorbent article 1.

Figure 6:
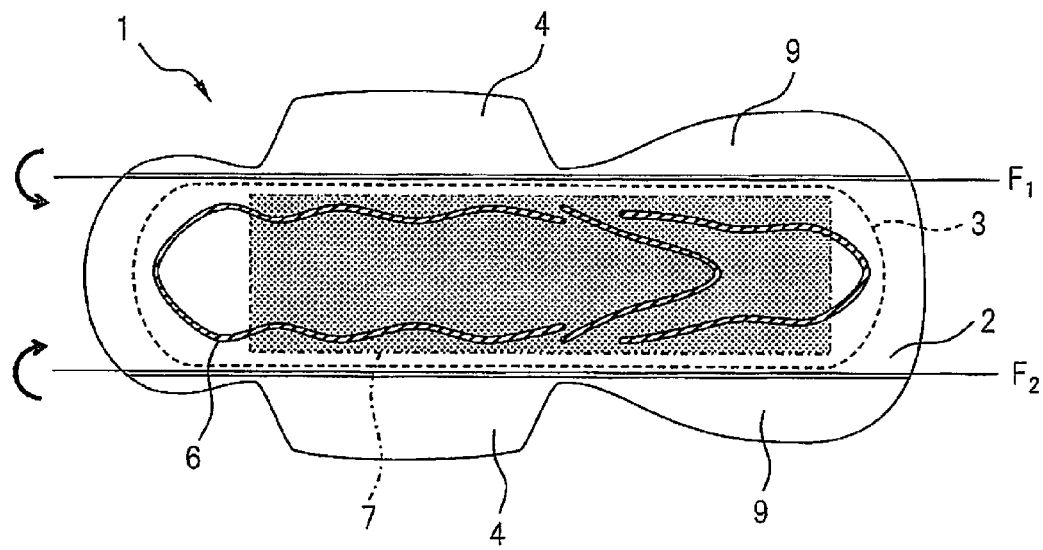
FIG. 6 is a diagram illustrating an example of production steps for the absorbent article 1 shown in FIG. 2.

FIG. 6 is a diagram illustrating an example of production steps for the absorbent article 1 shown in FIG. 2.

The absorbent article shown in FIG. 6 is the same as the absorbent article 1 shown in FIG. 2, except that the pair of side flaps 4 and the pair of hip flaps 9 do not include blood slipping agent-containing second regions 8. In FIG. 6, the side sheets are omitted for clarity of illustration.

An absorbent article 1 is prepared in which the top sheet 2 contains the blood slipping agent to be transferred to the pair of flaps 4, as shown in FIG. 6. More specifically, in the absorbent article 1 shown in FIG. 3, the excretory opening contact region of the top sheet 2, and the regions other than the excretory opening contact region, have a blood slipping agent-containing first region 7 containing the blood slipping agent that is to be transferred to the pair of flaps 4 and the pair of hip flaps 9. In consideration of transfer of a portion of the blood slipping agent, the blood slipping agent-containing first region 7 may be adjusted so as to contain a blood slipping agent with a greater basis weight than the final basis weight of the blood slipping agent.

Next, as indicated by the arrow in FIG. 6, the two side flaps 4 and the two hip flaps 9 are folded over onto the top sheet 2 along the axes $F_1$ and $F_2$ that are essentially parallel to the lengthwise direction of the absorbent article 1.

Figure 7:
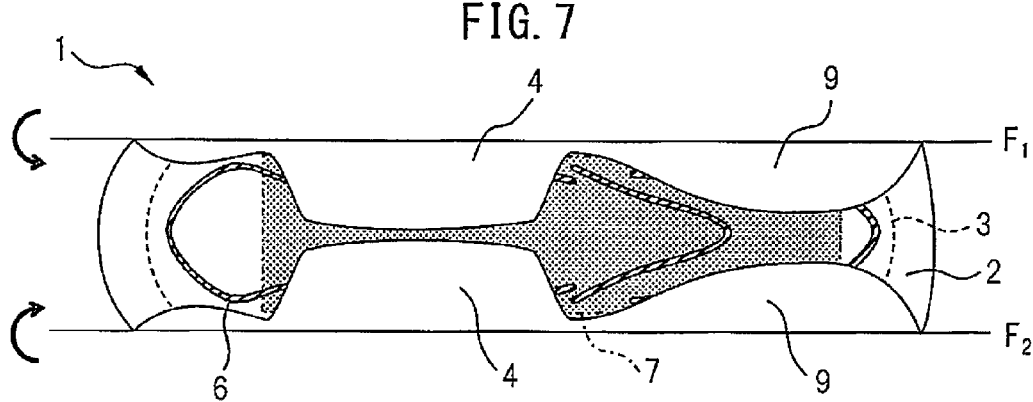
FIG. 7 is a diagram showing the absorbent article 1 in a state where two side flaps 4 and two hip flaps 9 are folded over onto the top sheet 2 along folding axes $F_1$ and $F_2$.

FIG. 7 is a diagram showing the absorbent article 1 in a state where two side flaps 4 and two hip flaps 9 are folded over onto the top sheet 2 along folding axes $F_1$ and $F_2$. After the two side flaps 4 have been folded over onto the top sheet 2, a portion of the blood slipping agent of the top sheet 2 migrates to the sections facing the side flaps 4, forming blood slipping agent-containing second regions 8. While the two side flaps 4 are being folded over, the two hip flaps 9 are folded over onto the top sheet 2 and a portion of the blood slipping agent of the top sheet 2 migrates to the sections facing the hip flaps 9, forming blood slipping agent-containing second regions 8.

The absorbent article 1 shown in FIG. 7 is the same as the absorbent article 1 shown in FIG. 2 when the two side flaps 4 and the two hip flaps 9 are reopened along the axes $F_1$ and $F_2$.

In order to transfer the blood slipping agent, the two side flaps 4 and the two hip flaps 9 may be actively pressed so that the top sheet 2 is in close contact with the two side flaps 4 and the two hip flaps 9 after folding over onto the top sheet 2 along the axes $F_1$ and $F_2$, but when the article is to be marketed as an individually packaged product after folding of the absorbent article and individual packaging, such pressing may be omitted. This is because the pressure applied during transport and storage of the absorbent article will allow the blood slipping agent of the top sheet to migrate into the two side flaps and the two hip flaps.

Figure 8:
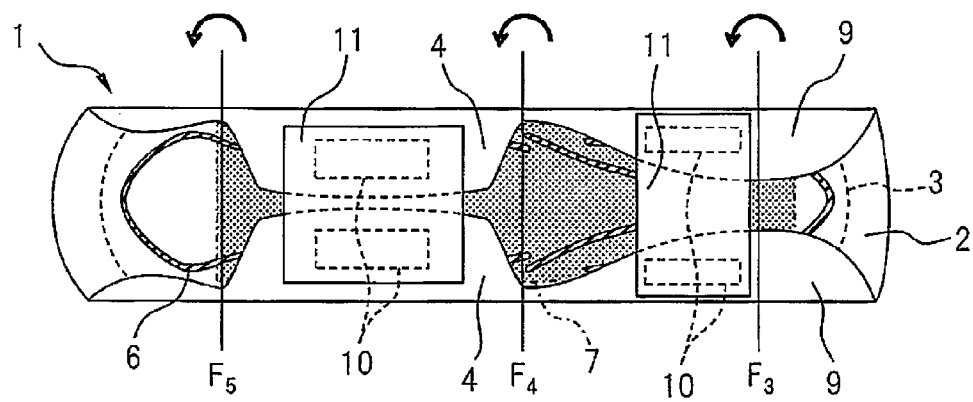
FIG. 8 is a diagram illustrating an example of an individual package of the absorbent article 1 shown in FIG. 7.

FIG. 8 is a diagram illustrating an example of an individual package of the absorbent article 1 shown in FIG. 7. In the absorbent article 1 shown in FIG. 7, an adhesive section 10, for anchoring the absorbent article 1 to the clothing of the wearer, and a release sheet 11, are attached to the surface of the clothing side sheet of the two side flaps 4 and the two hip flaps 9, forming an absorbent article 1 shown in FIG. 8. Next, the absorbent article 1 is folded along the folding axis $F_3$ so that the top sheet 2 is facing the inner side, as indicated by the right arrow in FIG. 8, the absorbent article 1 is folded along the folding axis $F_4$ so that the top sheet 2 is facing the inner side, as indicated by the center arrow in FIG. 8, the absorbent article 1 is folded along the folding axis $F_5$ so that the top sheet 2 is facing the inner side, as indicated by the left arrow in FIG. 8, and then the absorbent article 1 is individually packaged to produce a quadruple-folded individually packaged absorbent article 1.

In an embodiment where transfer is utilized to form blood slipping agent-containing second regions on the flaps, the location, size and shape of the blood slipping agent-containing second regions can be varied according to (1) the location, size and shape of the region of the top sheet that includes the blood slipping agent, (2) the locations, sizes and shapes of the flaps, and (3) the extent of folding of the flaps.

Also, in an embodiment where transfer is utilized to form blood slipping agent-containing second regions on the flaps, the basis weight of the blood slipping agent in the blood slipping agent-containing second regions can be adjusted by the strength of the pressure applied to bond the top sheet and the pair of flaps after the pair of flaps have been folded over onto the top sheet. A stronger pressure will result in more blood slipping agent migrating from the top sheet to the blood slipping agent-containing second regions, which will tend to approach the basis weight of the blood slipping agent in the blood slipping agent-containing first region.

When the blood slipping agent is to be transferred to the flaps by pressure, it is preferably applied with a pressure of preferably about 5 to about 100 $g/cm^2$, more preferably about 20 to about 100 $g/cm^2$, even more preferably about 40 to about 100 $g/cm^2$ and yet more preferably about 60 to about 100 $g/cm^2$, so that the top sheet and two side flaps are brought into close contact.

Any liquid-permeable top sheet that is commonly used in the art may be employed without any particular restrictions, and for example, it may be a sheet-like material having a structure that allows permeation of liquids, such as a porous film, woven fabric, nonwoven fabric or the like. The fibers composing such a woven fabric or nonwoven fabric may be natural fibers or chemical fibers, with examples of natural fibers including cellulose, such as ground pulp and cotton, and examples of chemical fibers including regenerated cellulose, such as rayon and fibril rayon, semi-synthetic cellulose, such as acetate and triacetate, thermoplastic hydrophobic chemical fibers, and hydrophilicized thermoplastic hydrophobic chemical fibers.

Examples of thermoplastic hydrophobic chemical fibers include polyethylene (PE), polypropylene (PP) and polyethylene terephthalate (PET) monofilaments, and fibers including PE and PP graft polymers.

Examples of nonwoven fabrics include air-through nonwoven fabrics, spunbond nonwoven fabrics, point bond nonwoven fabrics, spunlace nonwoven fabrics, needle punching nonwoven fabrics and meltblown nonwoven fabrics, as well as combinations thereof (such as SMS and the like).

Liquid-impermeable back sheets include films comprising PE and PP, air-permeable resin films, air-permeable resin films bonded to spunbond or spunlace nonwoven fabrics, and multilayer nonwoven fabrics, such as SMS. In consideration of flexibility of the absorbent article, a low-density polyethylene (LDPE) film with a basis weight of about 15-30 $g/m^2$, for example, is preferred.

An absorbent article according to another embodiment of this disclosure may include a second sheet between the liquid-permeable top sheet and the absorbent body. The second sheet may be any of the same examples as for the liquid-permeable top sheet.

The first example of the absorbent body is one having an absorbent core covered with a core wrap.

Examples of components for the absorbent core include hydrophilic fibers, including cellulose, such as ground pulp or cotton, regenerated cellulose, such as rayon or fibril rayon, semi-synthetic cellulose, such as acetate or triacetate, particulate polymers, filamentous polymers, thermoplastic hydrophobic chemical fibers, and hydrophilicized thermoplastic hydrophobic chemical fibers, as well as combinations thereof. The component of the absorbent core may also be a super absorbent polymer, such as granules of a sodium acrylate copolymer or the like.

The core wrap is not particularly restricted so long as it is a substance that is liquid-permeable and with a barrier property that does not allow permeation of the polymer absorber, and it may be a woven fabric or nonwoven fabric, for example. The woven fabric or nonwoven fabric may be made of a natural fiber, chemical fiber, tissue, or the like.

A second example of the absorbent body is one formed from an absorbing sheet or polymer sheet, with a thickness of preferably about 0.3-5.0 mm. The absorbing sheet or polymer sheet may usually be used without any particular restrictions so long as it is one that can be used in an absorbent article, such as a sanitary napkin.

The side sheet may be any of the same examples as for the liquid-permeable top sheet.

The flap can be formed from a side sheet and a liquid-impermeable back sheet, and optionally it may have a reinforcing sheet, such as paper, between them.

When the liquid-permeable top sheet is formed from a nonwoven fabric or woven fabric, the blood slipping agent or blood slipping agent-containing composition preferably does not obstruct the voids between the fibers of the nonwoven fabric or woven fabric, and for example, the blood slipping agent or blood slipping agent-containing composition may be attached as droplets or particulates on the surface of the nonwoven fabric or woven fabric fibers, or it may be covering the surfaces of the fibers.

On the other hand, when the liquid-permeable top sheet is formed of a porous film, the blood slipping agent or blood slipping agent-containing composition preferably does not occlude the pores of the porous film, and the blood slipping agent or the blood slipping agent-containing composition may either be attached to the surface of the porous film as droplets or particulates, or it may cover the surface of the film without occluding the pores. This is because if the blood slipping agent or blood slipping agent-containing composition obstructs the pores in the porous film, migration of the absorbed liquid into the absorbent body may be inhibited.

Furthermore, in order for the blood slipping agent or blood slipping agent-containing composition to slip down together with the absorbed menstrual blood, it preferably has a large surface area, and a blood slipping agent or blood slipping agent-containing composition present as droplets or particulates preferably has a small droplet/particle diameter.

The absorbent article according to another embodiment of this disclosure has a second sheet comprising a blood slipping agent or a blood slipping agent-containing composition. The absorbent article according to another embodiment of this disclosure has an absorbent body comprising a blood slipping agent or a blood slipping agent-containing composition.

When the material coated with the blood slipping agent or blood slipping agent-containing composition, for example, a top sheet, is a nonwoven fabric or woven fabric formed from a synthetic resin, or a porous film or the like, it is preferably subjected to hydrophilicizing treatment. The hydrophilicizing treatment may involve coating the surfaces of the fibers of the nonwoven fabric or woven fabric or the surface of the porous film with a hydrophilic agent, or mixing a hydrophilic agent with the synthetic resin used as the starting material for the nonwoven fabric or woven fabric or porous film.

This is because, if the material before coating of the blood slipping agent or blood slipping agent-containing composition is hydrophilic, there will be lipophilic regions due to the blood slipping agent, and hydrophilic regions due to the hydrophilic agent, that are sparsely dispersed on the top sheet, which will allow the blood slipping agent or blood slipping agent-containing composition to exhibit slipping performance and will facilitate rapid migration of menstrual blood into the absorbent body.

The blood slipping agent or blood slipping agent-containing composition also has an effect as a lubricant. Thus, when the top sheet is a nonwoven fabric or woven fabric, the blood slipping agent or blood slipping agent-containing composition reduces friction between the fibers and improves the flexibility. When the top sheet is a resin film, the blood slipping agent or blood slipping agent-containing composition can reduce friction between the top sheet and the skin.

An absorbent article according to a preferred embodiment of this disclosure is one that is intended for absorption of blood, such as a sanitary napkin or panty liner. An absorbent article according to a more preferred embodiment of this disclosure is an individually packaged, triple-folded or quadruple-folded sanitary napkin, panty liner or the like.

The absorbent article of this disclosure differs from known absorbent articles containing skin care compositions, lotion compositions and the like, in that it does not need components, such as emollients or immobilizing agents, and therefore the absorbent article according to one embodiment of this disclosure does not contain an emollient and/or immobilizing agent.

EXAMPLES

The present disclosure will now be explained in fuller detail by examples, with the understanding that it is not meant to be limited to the examples.

Example 1

Evaluation of Rewetting Rate and Absorbent Body Migration Rate

A commercially available sanitary napkin having the shape shown in FIG. 1 (not coated with a blood slipping agent) was prepared. The sanitary napkin was formed from a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150 to 450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The blood slipping agents used for testing are listed below.

[($a_1$) Ester of Chain Hydrocarbon Tetraol and at Least One Fatty Acid]

UNISTAR H-408BRS, product of NOF Corp.

Pentaerythritol tetra(2-ethylhexanoate), weight-average molecular weight: approximately 640

UNISTAR H-2408BRS-22, product of NOF Corp.

Mixture of pentaerythritol tetra(2-ethylhexanoate) and neopentylglycol di(2-ethylhexanoate) (58:42 as weight ratio), weight-average molecular weight: approximately 520

[($a_2$) Ester of Chain Hydrocarbon Triol and at Least One Fatty Acid]

Cetiol SB45DEO, Cognis Japan

Glycerin and fatty acid triester, with oleic acid or stearylic acid as the fatty acid.

SOY42, product of NOF Corp.

Glycerin and fatty acid triester with $C_{14}$ fatty acid: $C_{16}$ fatty acid: $C_{18}$ fatty acid:$C_{20}$ fatty acid (including both saturated fatty acids and unsaturated fatty acids) at a mass ratio of about 0.2:11:88:0.8, weight-average molecular weight: 880

Tri-C2L oil fatty acid glyceride, product of NOF Corp.

Glycerin and fatty acid triester with $C_8$ fatty acid:$C_{10}$ fatty acid:$C_{12}$ fatty acid at a weight ratio of about 37:7:56, weight-average molecular weight: approximately 570

Tri-CL oil fatty acid glyceride, product of NOF Corp.
  Glycerin and fatty acid triester with $C_8$ fatty acid:$C_{12}$ fatty acid at a weight ratio of about 44:56, weight-average molecular weight: approximately 570
PANACET 810s, product of NOF Corp.
  Glycerin and fatty acid triester with $C_8$ fatty acid:$C_{10}$ fatty acid at a mass ratio of about 85:15, weight-average molecular weight: approximately 480
PANACET 800, product of NOF Corp.
  Glycerin and fatty acid triester with octanoic acid ($C_8$) as the entire fatty acid portion, weight-average molecular weight: approximately 470
PANACET 800B, product of NOF Corp.
  Glycerin and fatty acid triester with 2-ethylhexanoic acid ($C_8$) as the entire fatty acid portion, weight-average molecular weight: approximately 470
NA36, product of NOF Corp.
  Glycerin and fatty acid triester with $C_{16}$ fatty acid:$C_{18}$ fatty acid:$C_{20}$ fatty acid (including both saturated fatty acids and unsaturated fatty acids) at a mass ratio of about 5:92:3, weight-average molecular weight: approximately 880
Tri-Coconut Fatty Acid Glyceride, product of NOF Corp.
  Glycerin and fatty acid triester with $C_8$ fatty acid: $C_{10}$ fatty acid:$C_{12}$ fatty acid:$C_{14}$ fatty acid:$C_{16}$ fatty acid (including both saturated fatty acids and unsaturated fatty acids) at a mass ratio of about 4:8:60:25:3, weight-average molecular weight: 670
Caprylic acid diglyceride, product of NOF Corp.
  Glycerin and fatty acid diester with octanoic acid as the fatty acid, weight-average molecular weight: approximately 340
[($a_3$) Ester of a Chain Hydrocarbon Diol and at Least One Fatty Acid]
UNISTAR H-208BRS, product of NOF Corp.
  Neopentyl glycol di(2-ethylhexanoate), weight-average molecular weight: approximately 360
COMPOL BL, product of NOF Corp.
  Dodecanoic acid ($C_{12}$) monoester of butylene glycol, weight-average molecular weight: approximately 270
COMPOL BS, product of NOF Corp.
  Octadecanoic acid ($C_{18}$) monoester of butylene glycol, weight-average molecular weight: approximately 350
[($c_2$) Ester of a Chain Hydrocarbon Tricarboxylic Acid, Hydroxy Acid, Alkoxy Acid or Oxoacid with 3 Carboxyl Groups, and at Least One Aliphatic Monohydric Alcohol]
Tributyl O-acetylcitrate, product of Tokyo Kasei Kogyo Co., Ltd.
  Weight-average molecular weight: approximately 400
Tributyl citrate, product of Tokyo Kasei Kogyo Co., Ltd.
  Weight-average molecular weight: approximately 360
[($c_3$) Ester of a Chain Hydrocarbon Dicarboxylic Acid, Hydroxy Acid, Alkoxy Acid or Oxoacid with 2 Carboxyl groups, and at least one aliphatic monohydric alcohol]
Dioctyl adipate, product of Wako Pure Chemical Industries, Ltd.
  Weight-average molecular weight: approximately 380
[($d_3$) Ester of a Fatty Acid and an Aliphatic Monohydric alcohol]
ELECTOL WE20, product of NOF Corp.
  Ester of dodecanoic acid ($C_{12}$) and dodecyl alcohol ($C_{12}$), weight-average molecular weight: approximately 360
ELECTOL WE40, product of NOF Corp.
  Ester of tetradecanoic acid ($C_{14}$) and dodecyl alcohol ($C_{12}$), weight-average molecular weight: approximately 390
[($e_1$) Polyoxy $C_3$-$C_6$ Alkylene Glycol]
UNIOL PB500, product of NOF Corp.
  Polybutylene glycol, weight-average molecular weight: approximately 500
UNIOL PB700, product of NOF Corp.
  Polyoxybutylene polyoxypropylene glycol, weight-average molecular weight: approximately 700
[($f_1$) Chain Alkane]
PARLEAM 6, product of NOF Corp.
  Branched chain hydrocarbon, produced by copolymerization of liquid isoparaffin, isobutene and n-butene followed by hydrogen addition, polymerization degree: approximately 5-10, weight-average molecular weight: approximately 330
[Other Materials]
NA50, product of NOF Corp.
  Glycerin and fatty acid triester obtained by addition of hydrogen to NA36 for reduced proportion of double bonds from unsaturated fatty acid starting material, weight-average molecular weight: approximately 880
(Caprylic acid/capric acid) monoglyceride, product of NOF Corp.
  Glycerin and fatty acid monoester, with octanoic acid ($C_8$) and decanoic acid ($C_{10}$) at a mass ratio of about 85:15, weight-average molecular weight: approximately 220
Monomuls 90-L2 lauric acid monoglyceride, product of Cognis Japan
Isopropyl citrate, product of Tokyo Kasei Kogyo Co., Ltd.
  Weight-average molecular weight: approximately 230
Diisostearyl malate
  Weight-average molecular weight: approximately 640
UNIOL PB1000R, product of NOF Corp.
  Polybutylene glycol, weight-average molecular weight: approximately 1,000
UNIOL D-250, product of NOF Corp.
  Polypropylene glycol, weight-average molecular weight: approximately 250
UNIOL D-400, product of NOF Corp.
  Polypropylene glycol, weight-average molecular weight: approximately 400
UNIOL D-700, product of NOF Corp.
  Polypropylene glycol, weight-average molecular weight: approximately 700
UNIOL D-1000, product of NOF Corp.
  Polypropylene glycol, weight-average molecular weight: approximately 1,000
UNIOL D-1200, product of NOF Corp.
  Polypropylene glycol, weight-average molecular weight: approximately 1,160
UNIOL D-2000, product of NOF Corp.
  Polypropylene glycol, weight-average molecular weight: approximately 2,030
UNIOL D-3000, product of NOF Corp.
  Polypropylene glycol, weight-average molecular weight: approximately 3,000
UNIOL D-4000, product of NOF Corp.
  Polypropylene glycol, weight-average molecular weight: approximately 4,000
PEG1500, product of NOF Corp.
  Polyethylene glycol, weight-average molecular weight: approximately 1,500-1,600
WILBRITE cp9, product of NOF Corp.
  Polybutylene glycol compound with OH groups at both ends esterified by hexadecanoic acid ($C_{16}$), weight-average molecular weight: approximately 1,150
UNILUBE MS-70K, product of NOF Corp.
  Stearyl ether of polypropylene glycol, approximately 15 repeating units, weight-average molecular weight: approximately 1,140

NONION S-6, product of NOF Corp.
Polyoxyethylene monostearate, approximately 7 repeating units, weight-average molecular weight: approximately 880
Unilube 5TP-300 KB
Polyoxyethylene polyoxypropylene pentaerythritol ether, produced by addition of 5 mol of ethylene oxide and 65 mol of propylene oxide to 1 mol of pentaerythritol, weight-average molecular weight: 4,130
WILBRITE s753, product of NOF Corp.
Polyoxyethylene polyoxypropylene polyoxybutylene glycerin, weight-average molecular weight: approximately 960
UNIOL TG-330, product of NOF Corp.
Glyceryl ether of polypropylene glycol, approximately 6 repeating units, weight-average molecular weight: approximately 330
UNIOL TG-1000, product of NOF Corp.
Glyceryl ether of polypropylene glycol, approximately 16 repeating units, weight-average molecular weight: approximately 1,000
UNIOL TG-3000, product of NOF Corp.
Glyceryl ether of polypropylene glycol, approximately 16 repeating units, weight-average molecular weight: approximately 3,000
UNIOL TG-4000, product of NOF Corp.
Glyceryl ether of polypropylene glycol, approximately 16 repeating units, weight-average molecular weight: approximately 4,000
UNILUBE DGP-700, product of NOF Corp.
Diglyceryl ether of polypropylene glycol, approximately 9 repeating units, weight-average molecular weight: approximately 700
UNIOX HC60, product of NOF Corp.
Polyoxyethylene hydrogenated castor oil, weight-average molecular weight: approximately 3,570
Vaseline, Product of Cognis Japan
Petroleum-Derived Hydrocarbon, Semi-Solid The kinematic viscosities, water holding percentages, weight-average molecular weights, IOBs and melting points of the samples are shown in Table 2.

For the melting point, "<45" indicates a melting point of below 45° C.

Almost the entire skin contact surface of the top sheet of the sanitary napkin was coated with the aforementioned blood slipping agent. Each blood slipping agent was used directly, when the blood slipping agent was liquid at room temperature, or when the blood slipping agent was solid at room temperature it was heated to a temperature of its melting point+20° C., and then a control seam HMA gun was used for atomization of each blood slipping agent and coating onto the skin contact surface of the top sheet to a basis weight of about 5 g/m².

Figure 10:
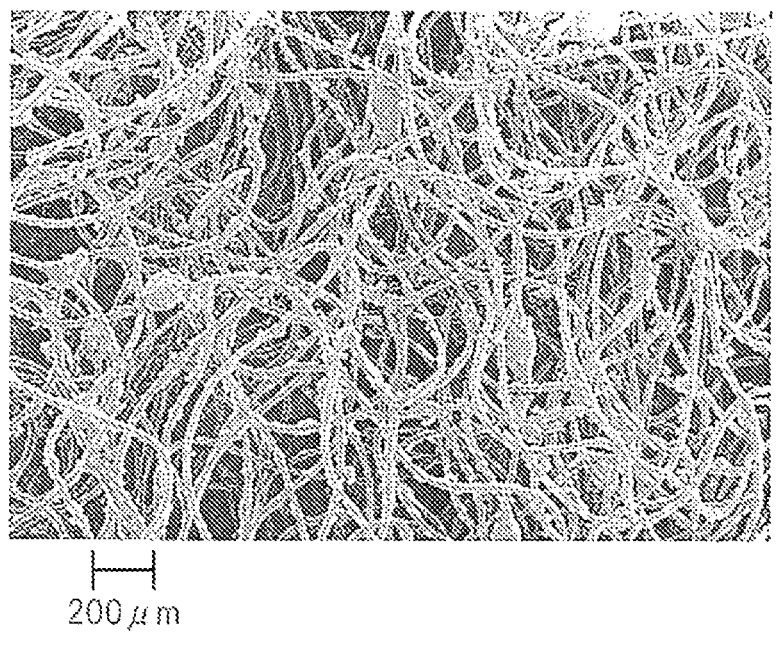
FIG. 10 is an electron micrograph of the skin contact surface of a top sheet in a sanitary napkin wherein the top sheet comprises tri-C2L oil fatty acid glycerides.

FIG. 10 is an electron micrograph of the skin contact surface of a top sheet in a sanitary napkin (No. 1-5) wherein the top sheet comprises tri-C2L oil fatty acid glycerides. As clearly seen in FIG. 10, the tri-C2L oil fatty acid glycerides are present on the fiber surfaces as fine particulates.

[Test Methods]

An acrylic board with an opened hole (200 mm×100 mm, 125 g, with a 40 mm×10 mm hole opened at the center) was placed on a top sheet comprising each blood slipping agent, and 3.0 g of horse EDTA blood at 37±1° C. (obtained by adding ethylenediaminetetraacetic acid (hereunder, "EDTA") to horse blood to prevent coagulation) was dropped through the hole using a pipette (once), and after 1 minute, 3.0 g of horse EDTA blood at 37±1° C. was again added dropwise through the acrylic board hole with a pipette (twice).

After the second dropping of blood, the acrylic board was immediately removed and 10 sheets of filter paper (Qualitative filter paper No. 2, product of Advantech Toyo, Inc., 50 mm×35 mm) (total weight of 10 filter sheets: $FW_D$ (g)) were placed on the location where the blood had been dropped, and then a weight was placed thereover at a pressure of 30 g/cm². After 1 minute, the filter paper was removed, the total weight $FW_1$ (g) of the 10 tested filter sheets was measured, and the "rewetting rate" was calculated by the following formula.

Rewetting rate (mass %)=100×[$FW_1$ (g)–$FW_0$ (g)]/6.0 (g)

In addition to the rewetting rate evaluation, the "absorbent body migration rate" was also measured as the time until migration of blood from the top sheet to the absorbent body after the second dropping of blood. The absorbent body migration rate is the time from introducing the blood onto the top sheet, until the redness of the blood could be seen on the surface and in the interior of the top sheet.

The results for the rewetting rate and absorbent body migration rate are shown below in Table 2.

The whiteness of the skin contact surface of the top sheet (TS) after the absorbent body migration rate test was visually evaluated on the following scale.

VG (Very Good): Virtually no redness of blood remaining, and no clear delineation between areas with and without blood.

G (Good): Slight redness of blood remaining, but difficult to discriminate between areas with and without blood.

F (Fair): Slight redness of blood remaining, areas with blood discernible.

P (Poor): Redness of blood completely remaining.

The tack on the skin contact surface of the top sheet was also measured at 35° C., and evaluated on the following scale.

G: No tack
F: Slight tack
P: Tack

The results are summarized in Table 2 below.

TABLE 2

| No. | Blood slipping agent | Kinematic viscosity (mm²/s, 40° C.) | Water holding percentage (mass %) | Wt.-average mol. wt. | IOB | Melting point (° C.) | Rewetting rate (%) | Absorbent body migration rate (sec) | TS whiteness | Tack |
|---|---|---|---|---|---|---|---|---|---|---|
| 1-1 | H-408BRS | 45 | 0.7 | 640 | 0.13 | <–5 | 1.2 | 3 | VG | G |
| 1-2 | H-2408BRS-22 | 22 | 0.8 | 520 | 0.18 | <–5 | 2.0 | 3 | VG | G |
| 1-3 | Cetiol SB45DEO | | | | 0.16 | 44 | 7.0 | 6 | VG | |
| 1-4 | SOY42 | | | 880 | 0.16 | 43 | 5.8 | 8 | VG | G |
| 1-5 | Tri-C2L oil fatty acid glyceride | 20 | <1.0 | 570 | 0.27 | 37 | 0.3 | 3 | VG | G |
| 1-6 | Tri-CL oil fatty acid glyceride | 15 | <1.0 | 570 | 0.28 | 38 | 1.7 | 3 | VG | G |

TABLE 2-continued

| No. | Blood slipping agent | Kinematic viscosity (mm²/s, 40° C.) | Water holding percentage (mass %) | Wt.-average mol. wt. | IOB | Melting point (° C.) | Rewetting rate (%) | Absorbent body migration rate (sec) | TS whiteness | Tack |
|---|---|---|---|---|---|---|---|---|---|---|
| 1-7 | PANACET 810s | 9 | 0.3 | 480 | 0.32 | −5 | 2.8 | 3 | VG | G |
| 1-8 | PANACET 800 | 15 | 0.5 | 470 | 0.33 | −5 | 0.3 | 3 | VG | G |
| 1-9 | PANACET 800B | 20 | 0.5 | 470 | 0.33 | −5 | 2.0 | 3 | VG | G |
| 1-10 | NA36 | 40 | <1.0 | 880 | 0.16 | 37 | 3.9 | 5 | VG | G |
| 1-11 | Tri-coconut oil fatty acid glyceride | 25 | <1.0 | 670 | 0.28 | 30 | 4.3 | 5 | VG | G |
| 1-12 | Caprylic acid diglyceride | 25 | 2.7 | 340 | 0.58 | <45 | 4.2 | 9 | G | G |
| 1-13 | UNISTAR H-208BRS | 8 | 0.7 | 360 | 0.24 | <−5 | 2.0 | 5 | VG | G |
| 1-14 | COMPOL BL | 10 | 1.6 | 270 | 0.50 | 2 | 2.0 | 5 | G | G |
| 1-15 | COMPOL BS | 35 | 0.3 | 350 | 0.36 | 37 | 7.9 | 9 | G | G |
| 1-16 | Tributyl O-acetylcitrate | 15 | 0.9 | 400 | 0.60 | <45 | 6.2 | 8 | VG | G |
| 1-17 | Tributyl citrate | 12 | 0.6 | 360 | 0.78 | <45 | 3.0 | 6 | G | G |
| 1-18 | Dioctyl adipate | 7 | 0.4 | 380 | 0.27 | <45 | 1.7 | 6 | VG | G |
| 1-19 | ELECTOL WE20 | 10 | 0.3 | 360 | 0.13 | 29 | 1.8 | 5 | VG | G |
| 1-20 | ELECTOL WE40 | 15 | 0.5 | 390 | 0.12 | 37 | 1.8 | 4 | VG | G |
| 1-21 | UNIOL PB500 | 40 | 3.6 | 500 | 0.44 | <45 | 4.5 | 4 | G | G |
| 1-22 | UNIOL PB700 | 50 | 2.3 | 700 | 0.49 | −5 | 2.8 | 5 | G | G |
| 1-23 | PARLEAM 6 | 5 | 0.06 | 330 | 0.00 | −5 | 6.0 | 8 | VG | G |
| 1-24 | NA50 | 80<< | —* | 880 | 0.18 | 52 | 15.5 | 60 | P | G |
| 1-25 | (Caprylic acid/ Capric acid) monoglyceride | 70 | 4.0<< | 220 | 1.15 | <45 | 4.0 | 4 | P | G |
| 1-26 | 90-L2 Lauric acid monoglyceride | 80<< | 4.0<< | <1,000 | 0.87 | 58 | 6.2 | 7 | P | G |
| 1-27 | Isopropyl citrate | 120 | 4.0<< | 230 | 1.56 | <45 | 12.2 | 5 | G | F |
| 1-28 | Diisostearyl malate | 450 | 4.0<< | 640 | 0.28 | <45 | 5.5 | 8 | F | F |
| 1-29 | UNIOL PB1000R | 70 | 5.5 | 1000 | 0.40 | <45 | 4.0 | 4 | G | F |
| 1-30 | UNIOL D-250 | 20 | 4.0<< | 250 | | <45 | — | — | P | G |
| 1-31 | UNIOL D-400 | 30 | 4.0<< | 400 | 0.76 | <45 | 8.7 | 40 | P | G |
| 1-32 | UNIOL D-700 | 50 | 34.6 | 700 | 0.58 | <45 | 7.5 | — | F | G |
| 1-33 | UNIOL D-1000 | 70 | 26.7 | 1,000 | 0.51 | <45 | 6.8 | 15 | F | F |
| 1-34 | UNIOL D-1200 | 90 | 16.2 | 1,160 | 0.48 | <45 | 0.5 | 11 | F | F |
| 1-35 | UNIOL D-2000 | 160 | | 2,030 | | <45 | — | — | F | P |
| 1-36 | UNIOL D-3000 | | 0.6 | 3,000 | 0.39 | <45 | 1.7 | 10 | F | P |
| 1-37 | UNIOL D-4000 | 450 | 0.5 | 4,000 | 0.38 | <45 | 1.0 | 7 | G | P |
| 1-38 | PEG1500 | 120 | 4.0<< | 1,500-1,600 | 0.78 | 40 | 11.0 | 38 | P | P |
| 1-39 | WILBRITE CP9 | 120 | 0.6 | 1,150 | 0.21 | 35 | 1.4 | 3 | G | P |
| 1-40 | UNILUBE MS-70K | 50 | 2.8 | 1,140 | 0.30 | <−10 | 6.7 | 3 | G | F |
| 1-41 | NONION S-6 | 65 | 4.0<< | 880 | 0.44 | 37 | 8.4 | 7 | P | G |
| 1-42 | UNILUBE 5TP-300KB | 310 | 3.9 | 4,130 | 0.39 | <45 | 2.0 | 6 | G | P |
| 1-43 | WILBRITE s753 | 120 | 27.3 | 960 | 0.67 | −5 | 9.3 | 9 | F | F |
| 1-44 | UNIOL TG-330 | 30 | | 330 | 1.27 | <45 | — | — | — | G |
| 1-45 | UNIOL TG-1000 | 100 | 21.2 | 1,000 | 0.61 | <45 | 14.2 | 7 | G | G |
| 1-46 | UNIOL TG-3000 | 230 | 4.3 | 3,000 | 0.42 | <45 | 0.8 | 6 | G | P |
| 1-47 | UNIOL TG-4000 | 300 | 2.4 | 4,000 | 0.40 | <45 | 2.0 | 6 | G | P |
| 1-48 | UNILUBE DGP-700 | 200 | 4.0<< | 700 | 0.91 | <0 | 8.0 | 10 | F | F |
| 1-49 | UNIOX HC60 | 1150 | | 3,570 | 0.46 | 33 | 14.6 | 46 | P | P |
| 1-50 | Vaseline | 80<< | 0.0 | <1,000 | 0.00 | 55 | 9.7 | 10 | F | P |
| 1-51 | None | — | — | — | — | — | 22.7 | 60< | P | G |

*High viscosity, unmeasurable.

In the absence of a blood slipping agent, the rewetting rate was 22.7% and the absorbent body migration rate was greater than 60 seconds, but the glycerin and fatty acid triesters all produced rewetting rates of no greater than 7.0% and absorbent body migration rates of no longer than 8 seconds, and therefore significantly improved the absorption performance.

Similarly, it was found that the absorption performance is greatly improved with a blood slipping agent having a kinematic viscosity of about 0.01 to 80 mm²/s at 40° C., a water holding percentage of about 0.01 to about 4.0 mass %, and a weight-average molecular weight of less than about 1,000.

Next, several volunteer participants were asked to wear sanitary napkins Nos. 1-1 to 1-51, and the obtained responses indicated that with the sanitary napkins comprising blood slipping agent Nos. 1-1 to 1-23, the top sheets had no sticky feel and the top sheets were smooth, even after absorption of menstrual blood.

Also, with sanitary napkins that comprised blood slipping agent Nos. 1-11, 1-13, 1-16, 1-18 to 1-20 and 1-23, the skin contact surfaces of the top sheets after absorption of menstrual blood was not reddened by the blood and the unpleasantness was minimal.

Also, a commercially available sanitary napkin having the same shape as shown in FIG. 1 (not coated with a blood slipping agent), was coated with the aforementioned blood slipping agent so as to have a blood slipping agent-containing first region and blood slipping agent-containing second regions in the regions shown in FIG. 1. The blood slipping agent was Coated using a control seam HMA gun, with heating to a temperature of the melting point+20° C. as necessary, so that the top sheet had the blood slipping agent at a basis weight of about 5 g/m² in the blood slipping agent-containing first region, and the flaps had the blood slipping agent at a basis weight of about 1 g/m² in the blood slipping agent-containing second regions.

Sanitary napkins No. 1'-1 (H-408BRS) to No. 1'-23 (PARLEAM 6) were prepared by these steps. Sanitary napkins No. 1'-1 and No. 1-1 were identical in that the blood slipping agent was H-408BRS, but the coating amounts were different. This also applies to the other sanitary napkins.

The produced sanitary napkins No. 1'-1 to 1'-23 were worn by several volunteer participants, and the responses indicated that with sanitary napkins No. 1'-1 to 1'-23, not only was menstrual blood rapidly absorbed into the absorbent body in the excretory opening contact region after absorption of menstrual blood, but even when a large amount of menstrual blood was absorbed and there was movement involving significant twisting of the body, the menstrual blood did not easily reach the side flaps and there was minimal seepage of menstrual blood from the side flaps.

Example 2

Surface Residue Rate of Menstrual Blood on Top Sheet with Ridge-Furrow Structure The surface residue rate of menstrual blood on a top sheet with a ridge-furrow structure was evaluated.

There were prepared a top sheet, formed of a hydrophilic agent-treated air-through nonwoven fabric (composite fiber composed of polyester and polyethylene terephthalate, basis weight: 35 g/m²), a second sheet, formed of an air-through nonwoven fabric (composite fiber composed of polyester and polyethylene terephthalate, basis weight: 30 g/m²), an absorbent body comprising pulp (basis weight: 150 to 450 g/m², increased at the center section), an acrylic super-absorbent polymer (basis weight: 15 g/m²) and tissue as a core wrap, a water-repellent agent-treated side sheet, and a back sheet composed of a polyethylene film.

The top sheet was a top sheet produced by the method described in Japanese Unexamined Patent Publication No. 2008-2034, having a ridge-furrow structure, with a ridge thickness of approximately 1.5 mm and a furrow thickness of approximately 0.4 mm, the pitch of the ridge-furrow structure (ridge width+furrow width) was approximately 4 mm, and open holes were formed in the furrows at an open area of approximately 15%.

UNISTAR H-408BRS (product of NOF Corp., tetraester of pentaerythritol and fatty acid) was selected as the blood slipping agent, and it was coated onto the skin contact surface (ridge-furrow side) of the top sheet from a control seam HMA gun at room temperature, to a basis weight of 5.0 g/m². With an electron microscope it was confirmed that the H-408BRS was adhering onto the fiber surfaces as fine particulates.

A back sheet, an absorbent body, a second sheet, and a top sheet with the ridge-furrow side facing upward, were stacked in that order to form sanitary napkin No. 2-1.

Sanitary napkins No. 2-2 to No. 2-40 were produced, changing the blood slipping agent from UNISTAR H-408BRS to the ones listed in Table 3. Each blood slipping agent was used directly, when it was liquid at room temperature, or when the blood slipping agent was solid at room temperature it was heated to its melting point of +20° C., and then a control seam HMA gun was used for atomization of the blood slipping agent and coating onto the skin contact surface of the top sheet to a basis weight of about 5 g/m².

The blood slipping agent was coated onto essentially the entire skin contact surface of the top sheet, and on both the ridges and furrows.

[Test Methods]

After measuring the weight: $W_2$ (g) of the top sheet (the weight of the top sheet before the test), an acrylic board with an opened hole (200 mm×100 mm, 125 g, with a 40 mm×10 mm hole opened at the center) was placed on the top sheet, at the center section in the lengthwise direction and widthwise direction of the absorbent article, and 4.0 g of horse EDTA blood at 37±1° C. (obtained by adding ethylenediaminetetraacetic acid (hereunder, "EDTA") to horse blood to prevent coagulation) was dropped through the hole using a pipette.

After dropping the horse EDTA blood, the acrylic board was immediately removed, the top sheet was taken off, the mass $W_3$ (g) (mass of the top sheet after the test) was measured and the "surface residue rate A (mass %)" was calculated by the following formula.

Surface residue rate (mass %)=100×[$W_3$ (g)−$W_2$ (g)]/ 4.0 (g)

The results are shown in Table 3 below.

TABLE 3

| No. | Blood slipping agent | Surface residue rate (mass %) |
|---|---|---|
| 2-1 | H-408BRS | 0.8 |
| 2-2 | H-2408BRS-22 | 0.8 |
| 2-3 | PANACET 810s | 0.8 |
| 2-4 | PANACET 800 | 1.8 |
| 2-5 | Caprylic acid diglyceride | 1.0 |
| 2-6 | UNISTAR H-208BRS | 0.5 |
| 2-7 | COMPOL BL | 1.3 |
| 2-8 | COMPOL BS | 2.5 |
| 2-9 | Tributyl O-acetylcitrate | 0.5 |
| 2-10 | Tributyl citrate | 1.8 |
| 2-11 | Dioctyl adipate | 1.5 |
| 2-12 | ELECTOL WE20 | 0.5 |
| 2-13 | ELECTOL WE40 | 2.3 |
| 2-14 | UNIOL PB500 | 2.5 |
| 2-15 | UNIOL PB700 | 1.3 |
| 2-16 | PARLEAM 6 | 2.0 |
| 2-17 | NA50 | 4.3 |
| 2-18 | (Caprylic acid/Capric acid) monoglyceride | 5.0 |
| 2-19 | 90-L2 Lauric acid monoglyceride | 5.0 |
| 2-20 | Isopropyl citrate | 4.8 |
| 2-21 | Diisostearyl malate | 3.3 |
| 2-22 | UNIOL PB1000R | 2.5 |
| 2-23 | UNIOL D-250 | 3.8 |
| 2-24 | UNIOL D-400 | 4.8 |
| 2-25 | UNIOL D-700 | 4.8 |
| 2-26 | UNIOL D-1000 | 3.8 |
| 2-27 | UNIOL D-1200 | 3.0 |
| 2-28 | UNIOL D-3000 | 3.0 |
| 2-29 | UNIOL D-4000 | 2.5 |
| 2-30 | PEG1500 | 5.5 |
| 2-31 | WILBRITE CP9 | 6.8 |
| 2-32 | UNILUBE MS-70K | 1.5 |
| 2-33 | UNILUBE 5TP-300KB | 2.0 |
| 2-34 | WILBRITE s753 | 3.5 |
| 2-35 | UNIOL TG-1000 | 3.5 |
| 2-36 | UNIOL TG-3000 | 1.0 |
| 2-37 | UNIOL TG-4000 | 2.0 |
| 2-38 | UNILUBE DGP-700 | 3.5 |
| 2-39 | Vaseline | 4.0 |
| 2-40 | None | 7.5 |

With sanitary napkin No. 2-40, which had no blood slipping agent, the surface residue rate was 7.5 mass %, but with sanitary napkins No. 2-1 to No. 2-16 wherein the kinematic viscosity and water holding percentage were within the prescribed ranges, the surface residue rate was 2.5 mass % or lower.

With sanitary napkins No. 2-1 to No. 2-16, it was observed that the horse EDTA blood that was dropped onto the ridges of the top sheet slipped down from the ridges into the furrows, and was rapidly absorbed from the furrows into the absorbent body. However, with sanitary napkin No. 2-40 which had no blood slipping agent, the dropped horse EDTA blood did not slip down into the furrows but slowly dripped down into the furrows, most of it remaining on the ridges of the top sheet. Also, with the absorbent articles with high water holding percentage, as with No. 2-25, for example, the horse EDTA blood that was dropped onto the ridges of the top sheet did not slip down into the furrows but slowly dripped while partially remaining on the top sheet, and a portion thereof remained on the ridges.

The following experiment was also conducted in order to confirm the function of the blood slipping agent.

Example 3

Viscosity of Blood Containing Blood Slipping Agent

The viscosity of the blood slipping agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 μm, and the viscosity was measured at 37±0.5° C. The sample was not subjected to a uniform shear rate due to the parallel plate, but the average shear rate indicated by the device was $10\ s^{-1}$.

The viscosity of the horse defibrinated blood containing 2 mass % PANACET 810s was 5.9 mPa·s, while the viscosity of the horse defibrinated blood containing no blood slipping agent was 50.4 mPa·s. Thus, the horse defibrinated blood containing 2 mass % PANACET 810s clearly had an approximately 90% lower viscosity than the blood containing no blood slipping agent.

It is known that blood contains components, such as blood cells and has a thixotropic nature, and it is believed that the blood slipping agent of the present disclosure has an effect of lowering the viscosity of blood, such as menstrual blood in the low viscosity range. Lowering the blood viscosity presumably allows absorbed menstrual blood to more easily migrate rapidly from the top sheet to the absorbent body.

Example 4

Photomicrograph of Blood Slipping Agent-Containing Blood

Menstrual blood was sampled from healthy volunteers onto thin plastic wrap, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood slipping agent is shown in FIG. 11(a), and a photomicrograph of menstrual blood containing PANACET 810s is shown in FIG. 11(b).

Figure 11:
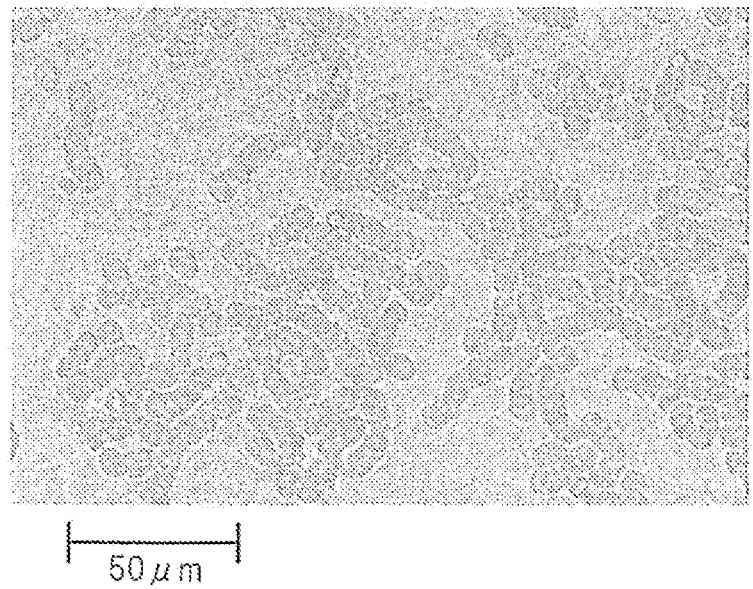
FIG. 11 is a pair of photomicrographs of menstrual blood containing and not containing a blood slipping agent.
Figure 11:
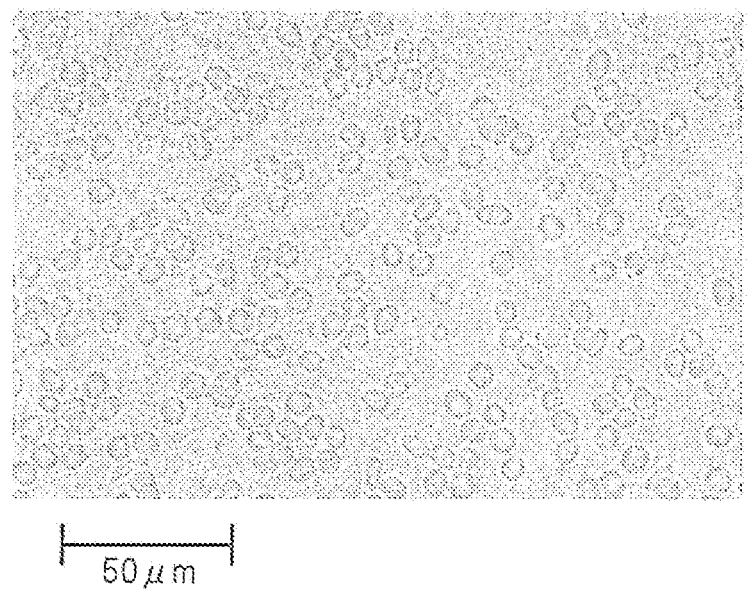

From FIGS. 11(a) and 11(b), it is seen that the erythrocytes formed aggregates, such as rouleaux in the menstrual blood containing no blood slipping agent, while the erythrocytes were stably dispersed in the menstrual blood containing PANACET 810s. This suggests that the blood slipping agent functions to stabilize erythrocytes in blood.

Example 5

Surface Tension of Blood Containing Blood Slipping Agent

The surface tension of blood containing a blood slipping agent was measured by the pendant drop method, using a Drop Master500 contact angle meter by Kyowa Interface Science Co., Ltd. The surface tension was measured after adding a prescribed amount of blood slipping agent to sheep defibrinated blood, and thoroughly shaking.

Figure 12:
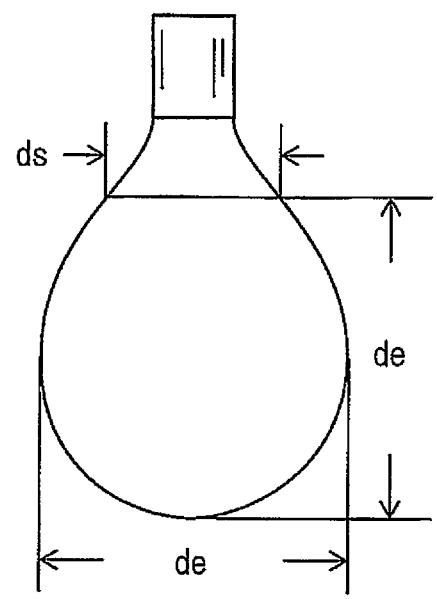
FIG. 12 is a diagram illustrating a method of measuring surface tension.

The measurement was accomplished automatically with a device, and the surface tension γ was determined by the following formula (see FIG. 12).

$$\gamma = g \times \rho \times (de)^2 \times 1/H$$

g: Gravitational constant
1/H: Correction factor determined from ds/de
ρ: Density
de: Maximum diameter
ds: Diameter at location of increase by de from dropping edge The density ρ was measured at the temperatures listed in Table 4, according to JIS K 2249-1995, "Density test methods and density/mass/volume conversion tables", "5. Vibrating density test method".

The measurement was accomplished using a DA-505 by Kyoto Electronics Co., Ltd.

The results are shown in Table 4 below.

TABLE 4

| No. | Blood slipping agent Type | Amount (mass %) | Measuring temperature (° C.) | Surface tension (mN/m) |
|---|---|---|---|---|
| 5-1 | — | — | 35 | 62.1 |
| 5-2 | PANACET | 0.01 | 35 | 61.5 |
| 5-3 | 810s | 0.05 | 35 | 58.2 |
| 5-4 |  | 0.10 | 35 | 51.2 |
| 5-5 | ELECTOL WE20 | 0.10 | 35 | 58.8 |
| 5-6 | PARLEAM 6 | 0.10 | 35 | 57.5 |
| 5-7 | — | — | 50 | 56.3 |
| 5-8 | WILBRITE cp9 | 0.10 | 50 | 49.1 |

Based on Table 4 it is seen that the blood slipping agent has an effect of lowering the surface tension of blood.

Lowering the surface tension of blood presumably allows absorbed blood to rapidly migrate from the top sheet to the absorbent body, without being retained between the top sheet fibers.

The present disclosure relates to the following J1 to J15.
[J1]
An absorbent article having a liquid-permeable top sheet, a liquid-impermeable back sheet and an absorbent body between the top sheet and the back sheet,
wherein the absorbent article comprises, at both sides in a lengthwise direction, a pair of flaps for anchoring the absorbent article to a clothing of a wearer,
at least an excretory opening contact region of the top sheet and the pair of flaps have a blood slipping agent-containing first region and blood slipping agent-containing second regions each containing a blood slipping agent with a kinematic viscosity of 0.01 to 80 mm²/s at 40° C., a water holding percentage of 0.01 to 4.0 mass % and a weight-average molecular weight of less than 1,000, a basis weight of the blood slipping agent in the blood slipping agent-containing first region in the excretory opening contact region of the top sheet is greater than a basis weight of the blood slipping agent in the blood slipping agent-containing second regions of the pair of flaps.

[J2]

The absorbent article according to J1, wherein the blood slipping agent further has an IOB of 0.00 to 0.60.

[J3]

The absorbent article according to claim 1 or 2, wherein the pair of flaps are folded over onto the top sheet.

[J4]

The absorbent article according to any one of J1 to J3, wherein at least a portion of the blood slipping agent in the pair of flaps is coated by transferring a portion of the blood slipping agent in the top sheet.

[J5]

The absorbent article according to any one of J1 to J4, wherein the top sheet has the blood slipping agent at a basis weight of 1 to 30 g/m² in the excretory opening contact region.

[J6]

The absorbent article according to any one of J1 to J5, wherein the pair of flaps has the blood slipping agent at a basis weight of 1 to 70 mass % of the basis weight of the blood slipping agent in the excretory opening contact region of the top sheet.

[J7]

The absorbent article according to any one of J1 to J6, wherein the pair of flaps includes a pair of side flaps and a pair of hip flaps, and the blood slipping agent-containing second region is formed in the pair of side flaps and/or the pair of hip flaps.

[J8]

The absorbent article according to any one of J1 to J7, wherein the blood slipping agent is selected from the group consisting of following items (i) to (iii), and any combination thereof:

(i) a hydrocarbon;

(ii) a compound having (ii-1) a hydrocarbon moiety and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—), inserted between a C—C single bond of the hydrocarbon moiety, and (iii-3) one or more, same or different groups selected from the group consisting of carboxyl group (—COOH) and hydroxyl group (—OH), substituting a hydrogen on the hydrocarbon moiety;

with the proviso that when two or more oxy groups are inserted in the compound of (ii) or (iii), the oxy groups are not adjacent.

[J9]

The absorbent article according to any one of J1 to J8, wherein the blood slipping agent is selected from the group consisting of following items (1') to (iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same, or different groups selected from the group consisting of carboxyl group (—COOH) and hydroxyl group (—OH) substituting a hydrogen on the hydrocarbon moiety;

with the proviso that when two or more same or different bonds are inserted in the compound of (ii') or (iii'), the bonds are not adjacent.

[J10]

The absorbent article according to any one of J1 to J9, wherein the blood slipping agent is selected from the group consisting of following items (A) to (F), as well as any combination thereof:

(A) an ester of (A1) a compound having a chain hydrocarbon moiety and 2-4 hydroxyl groups substituting hydrogens on the chain hydrocarbon moiety, and (A2) a compound having a chain hydrocarbon moiety and one carboxyl group substituting a hydrogen on the chain hydrocarbon moiety;

(B) an ether of (B1) a compound having a chain hydrocarbon moiety and 2-4 hydroxyl groups substituting hydrogens on the chain hydrocarbon moiety, and (B2) a compound having a chain hydrocarbon moiety and one hydroxyl group substituting a hydrogen on the chain hydrocarbon moiety;

(C) an ester of (C1) a carboxylic acid, hydroxy acid, alkoxy acid or oxoacid containing a chain hydrocarbon moiety and 2-4 carboxyl groups substituting hydrogens on the chain hydrocarbon moiety, and (C2) a compound having a chain hydrocarbon moiety and one hydroxyl group substituting a hydrogen on the chain hydrocarbon moiety;

(D) a compound having a chain hydrocarbon moiety, and one bond selected from the group consisting of ether bond (—O—), carbonyl bond (—CO—), ester bond (—COO—) and carbonate bond (—OCOO—), inserted between a C—C single bond of the chain hydrocarbon moiety;

(E) a polyoxy $C_3$-$C_6$ alkylene glycol, or alkyl ester or alkyl ether thereof; and (F) a chain hydrocarbon.

[J11]

The absorbent article according to any one of J1 to J10, wherein the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, (e₂) an ester of a polyoxy $C_3$-$C_6$ alkylene glycol and at least one fatty acid, (e₃) an ether of a polyoxy $C_3$-$C_6$ alkylene glycol and at least one aliphatic monohydric alcohol, and (f₁) a chain alkane, as well as any combination thereof.

[J12]

The absorbent article according to any one of J1 to J11, wherein the top sheet and skin side sheet of the pair of flaps are each selected from the group consisting of nonwoven fabric, woven fabric and porous film, and the blood slipping agent adheres as droplets or particulates on surfaces of fibers of the nonwoven fabric or woven fabric, or on surface of the porous film.

[J13]

The absorbent article according to any one of J1 to J12, which is an individually packaged sanitary napkin or panty liner.

[J14]

A method for producing an absorbent article according to any one of J1 to J13, comprising the steps of:

providing an absorbent article wherein the liquid-permeable top sheet contains a blood slipping agent to be transferred to a pair of flaps, and transferring a portion of the blood slipping agent of the top sheet to the pair of flaps by folding the pair of flaps over onto the top sheet.

[J15]

The method according to J14, further comprising a step of coating the liquid-permeable top sheet with a blood slipping agent or blood slipping agent-containing composition to be transferred to the pair of flaps.

REFERENCE SIGNS LIST

1 Absorbent article
2 Top sheet
3 Absorbent body
4 Side flap
5 Side sheet
6, 6' Embossings
7 Blood slipping agent-containing first region
8 Blood slipping agent-containing second region
9 Hip flap
10 Adhesive section
11 Release sheet
21 Back sheet
22 Skin contact surface
23 Projection
24 Recess
25 Blood slipping agent
26, 26', 26" Menstrual blood

The invention claimed is:

1. An absorbent article having a liquid-permeable top sheet, a liquid-impermeable back sheet and an absorbent body between the top sheet and the back sheet, wherein the absorbent article comprises, at both sides in a lengthwise direction, a pair of flaps for anchoring the absorbent article to a clothing of a wearer, at least an excretory opening contact region of the top sheet and the pair of flaps have a blood slipping agent-containing first region and blood slipping agent-containing second regions each containing a blood slipping agent with a kinematic viscosity of 0.01 to 80 mm²/s at 40° C., a water holding percentage of 0.01 to 4.0 mass % and a weight-average molecular weight of less than 1,000, a basis weight of the blood slipping agent in the blood slipping agent-containing first region in the excretory opening contact region of the top sheet is greater than a basis weight of the blood slipping agent in the blood slipping agent-containing second regions of the pair of flaps.

2. The absorbent article according to claim 1, wherein the blood slipping agent further has an IOB of 0.00 to 0.60.

3. The absorbent article according to claim 1, wherein the pair of flaps are folded over onto the top sheet.

4. The absorbent article according to claim 1, wherein at least a portion of the blood slipping agent in the pair of flaps is coated by transferring a portion of the blood slipping agent in the top sheet.

5. The absorbent article according to claim 1, wherein the top sheet has the blood slipping agent at a basis weight of 1 to 30 g/m² in the excretory opening contact region.

6. The absorbent article according to claim 1, wherein the pair of flaps has the blood slipping agent at a basis weight of 1 to 70 mass % of the basis weight of the blood slipping agent in the excretory opening contact region of the top sheet.

7. The absorbent article according to claim 1, wherein the pair of flaps includes a pair of side flaps and a pair of hip flaps, and the blood slipping agent-containing second region is formed in the pair of side flaps and/or the pair of hip flaps.

8. The absorbent article according to claim 1, wherein the blood slipping agent is selected from the group consisting of following items (i) to (iii), and any combination thereof:

(i) a hydrocarbon;

(ii) a compound having (ii-1) a hydrocarbon moiety and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—), inserted between a C—C single bond of the hydrocarbon moiety, and (iii-3) one or more, same or different groups selected from the group consisting of carboxyl group (—COOH) and hydroxyl group (—OH), substituting a hydrogen on the hydrocarbon moiety;

with the proviso that when two or more oxy groups are inserted in the compound of (ii) or (iii), the oxy groups are not adjacent.

9. The absorbent article according to claim 1, wherein the blood slipping agent is selected from the group consisting of following items (i) to (iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting a hydrogen on the hydrocarbon moiety;

with the proviso that when two or more same or different bonds are inserted in the compound of (ii) or (iii'), the bonds are not adjacent.

10. The absorbent article according to claim 1, wherein the blood slipping agent is selected from the group consisting of following items (A) to (F), as well as any combination thereof:
- (A) an ester of (A1) a compound having a chain hydrocarbon moiety and 2-4 hydroxyl groups substituting hydrogens on the chain hydrocarbon moiety, and (A2) a compound having a chain hydrocarbon moiety and one carboxyl group substituting a hydrogen on the chain hydrocarbon moiety;
- (B) an ether of (B1) a compound having a chain hydrocarbon moiety and 2-4 hydroxyl groups substituting hydrogens on the chain hydrocarbon moiety, and (B2) a compound having a chain hydrocarbon moiety and one hydroxyl group substituting a hydrogen on the chain hydrocarbon moiety;
- (C) an ester of (C1) a carboxylic acid, hydroxy acid, alkoxy acid or oxoacid containing a chain hydrocarbon moiety and 2-4 carboxyl groups substituting hydrogens on the chain hydrocarbon moiety, and (C2) a compound having a chain hydrocarbon moiety and one hydroxyl group substituting a hydrogen on the chain hydrocarbon moiety;
- (D) a compound having a chain hydrocarbon moiety, and one bond selected from the group consisting of ether bond (—O—), carbonyl bond (—CO—), ester bond (—COO—) and carbonate bond (—OCOO—), inserted between a C—C single bond of the chain hydrocarbon moiety;
- (E) a polyoxy $C_3$-$C_6$ alkylene glycol, or alkyl ester or alkyl ether thereof; and
- (F) a chain hydrocarbon.

11. The absorbent article according to claim 1, wherein the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycol and at least one fatty acid, ($e_3$) an ether of a polyoxy $C_3$-$C_6$ alkylene glycol and at least one aliphatic monohydric alcohol, and ($f_1$) a chain alkane, as well as any combination thereof.

12. The absorbent article according to claim 1, wherein the top sheet and skin side sheet of the pair of flaps are each selected from the group consisting of nonwoven fabric, woven fabric and porous film, and the blood slipping agent adheres as droplets or particulates on surfaces of fibers of the nonwoven fabric or woven fabric, or on surface of the porous film.

13. The absorbent article according to claim 1, which is an individually packaged sanitary napkin or panty liner.

14. A method for producing an absorbent article according to claim 1, comprising the steps of:
- providing an absorbent article wherein the liquid-permeable top sheet contains a blood slipping agent to be transferred to a pair of flaps, and
- transferring a portion of the blood slipping agent of the top sheet to the pair of flaps by folding the pair of flaps over onto the top sheet.

15. The method according to claim 14, further comprising a step of coating the liquid-permeable top sheet with a blood slipping agent or blood slipping agent-containing composition to be transferred to the pair of flaps.

* * * * *